(12) United States Patent
Olsen et al.

(10) Patent No.: US 7,575,575 B2
(45) Date of Patent: *Aug. 18, 2009

(54) ADJUSTABLE SPLINT FOR OSTEOSYNTHESIS WITH MODULAR COMPONENTS

(75) Inventors: Ron Anthon Olsen, Kingman, AZ (US); Daniel E. Gerbec, Logan, UT (US)

(73) Assignee: Ron Anthon Olsen, Kingman, AZ (US)

( * ) Notice: Subject to any disclaimer, the term of this patent is extended or adjusted under 35 U.S.C. 154(b) by 97 days.

This patent is subject to a terminal disclaimer.

(21) Appl. No.: 11/084,056

(22) Filed: Mar. 18, 2005

(65) Prior Publication Data

US 2006/0229604 A1    Oct. 12, 2006

(51) Int. Cl.
    A61F 5/04    (2006.01)
(52) U.S. Cl. ............................................ 606/57; 606/59
(58) Field of Classification Search .............. 606/54–59
    See application file for complete search history.

(56) References Cited

U.S. PATENT DOCUMENTS

| | | | |
|---|---|---|---|
| 1,201,864 A | 10/1916 | OverMeyer | |
| 1,789,060 A | 1/1931 | Weisenbach | |
| 1,869,726 A | 8/1932 | Youngren | |
| 1,997,466 A | 4/1935 | Longfellow | |
| 2,020,262 A | 11/1935 | Longfellow | |
| 2,024,325 A | 12/1935 | Allen | |
| 2,238,870 A | 4/1941 | Haynes | |
| 2,250,417 A | 7/1941 | Ettinger | |
| 2,251,209 A | 7/1941 | Stader | |
| 2,371,519 A | 3/1945 | Haynes | |
| 2,388,482 A | 11/1945 | Haynes | |
| 2,391,537 A | 12/1945 | Anderson | |
| 2,393,694 A | 1/1946 | Kirschner | |
| 2,406,987 A | 9/1946 | Anderson | |
| 2,435,850 A | 2/1948 | Siebrandt | |
| 2,439,995 A | 4/1948 | Thrailkill | |
| 3,877,424 A | 4/1975 | Murray | |
| 3,976,060 A * | 8/1976 | Hildebrandt et al. | ........ 606/241 |
| 4,098,269 A | 7/1978 | Judet | |

(Continued)

FOREIGN PATENT DOCUMENTS

DE    3722595    1/1989

(Continued)

OTHER PUBLICATIONS

Final Office Action for related case U.S. Appl. No. 11/083,566, mailed Nov. 14, 2008.*

(Continued)

*Primary Examiner*—Eduardo C Robert
*Assistant Examiner*—Jerry Cumberledge
(74) *Attorney, Agent, or Firm*—Workman Nydegger

(57) ABSTRACT

Adjustable splints for treating bone breaks and fractures provide a variety of different options for adjusting the locations and configurations of the splints. Adjustable mounts on the splints can be moved to a variety of different locations with respect to the splint main body housings and bone connectors can be rotated into a variety of positions within the mounts. Main bodies of the splint devices can be conveniently moved with respect to each other into a variety of different configurations and positions.

25 Claims, 22 Drawing Sheets

U.S. PATENT DOCUMENTS

| | | |
|---|---|---|
| 4,258,708 A | 3/1981 | Gentile |
| 4,273,116 A | 6/1981 | Chiquet |
| 4,312,336 A | 1/1982 | Danieletto et al. |
| 4,456,004 A | 6/1984 | Kenny |
| 4,483,334 A | 11/1984 | Murray |
| RE31,809 E | 1/1985 | Danieletto et al. |
| 4,502,473 A | 3/1985 | Harris et al. |
| 4,554,915 A | 11/1985 | Brumfield |
| 4,570,625 A | 2/1986 | Harris et al. |
| 4,604,997 A | 8/1986 | De Bastiani et al. |
| 4,611,586 A | 9/1986 | Agee et al. |
| 4,621,627 A | 11/1986 | DeBastiani et al. |
| 4,628,919 A | 12/1986 | Clyburn |
| 4,628,921 A | 12/1986 | Rousso |
| 4,643,177 A | 2/1987 | Sheppard et al. |
| 4,662,365 A | 5/1987 | Gotzen et al. |
| 4,782,842 A | 11/1988 | Fietti, Jr. |
| 4,828,277 A | 5/1989 | De Bastiani et al. |
| 4,848,368 A | 7/1989 | Kronner |
| 4,895,141 A | 1/1990 | Koeneman et al. |
| 4,919,119 A | 4/1990 | Jonsson et al. |
| 4,920,959 A | 5/1990 | Witzel et al. |
| 4,922,896 A | 5/1990 | Agee et al. |
| 4,946,179 A | 8/1990 | De Bastiani et al. |
| 4,968,316 A | 11/1990 | Hergenroeder |
| 4,988,349 A * | 1/1991 | Pennig .................. 606/58 |
| 5,019,077 A | 5/1991 | De Bastiani et al. |
| 5,026,374 A | 6/1991 | Dezza et al. |
| 5,047,029 A * | 9/1991 | Aebi et al. .................. 606/61 |
| 5,062,853 A * | 11/1991 | Forte .................. 623/22.2 |
| 5,074,865 A | 12/1991 | Fahmy |
| 5,098,432 A | 3/1992 | Wagenknecht |
| 5,108,394 A | 4/1992 | Kurokawa |
| 5,122,140 A | 6/1992 | Asche et al. |
| 5,122,145 A | 6/1992 | Fishbane |
| 5,152,280 A | 10/1992 | Danieli |
| 5,160,335 A | 11/1992 | Wagenknecht |
| 5,167,661 A | 12/1992 | Wagenknecht |
| 5,196,014 A | 3/1993 | Lin |
| 5,207,676 A | 5/1993 | Canadell et al. |
| 5,261,909 A | 11/1993 | Sutterlin et al. |
| 5,281,224 A | 1/1994 | Faccioli et al. |
| 5,292,322 A | 3/1994 | Faccioli et al. |
| 5,301,177 A | 4/1994 | Kumakura |
| 5,304,177 A | 4/1994 | Pennig |
| 5,318,571 A | 6/1994 | Benson |
| 5,320,622 A | 6/1994 | Faccioli et al. |
| 5,320,623 A | 6/1994 | Pennig |
| 5,330,474 A | 7/1994 | Lin |
| 5,334,202 A | 8/1994 | Carter |
| 5,342,360 A | 8/1994 | Faccioli et al. |
| 5,376,090 A | 12/1994 | Pennig |
| 5,382,248 A | 1/1995 | Jacobson et al. |
| 5,397,322 A | 3/1995 | Campopiano |
| 5,405,347 A | 4/1995 | Lee et al. |
| RE34,985 E | 6/1995 | Pennig |
| 5,429,637 A | 7/1995 | Hardy |
| 5,433,720 A | 7/1995 | Faccioli et al. |
| 5,437,667 A | 8/1995 | Papierski et al. |
| 5,443,465 A | 8/1995 | Pennig |
| 5,451,225 A | 9/1995 | Ross, Jr. et al. |
| 5,454,810 A | 10/1995 | Pohl et al. |
| 5,540,688 A | 7/1996 | Navas |
| 5,545,162 A | 8/1996 | Huebner |
| 5,591,164 A | 1/1997 | Nazre et al. |
| 5,601,551 A | 2/1997 | Taylor et al. |
| 5,603,717 A | 2/1997 | Benson |
| 5,611,800 A * | 3/1997 | Davis et al. .................. 606/61 |
| 5,620,442 A | 4/1997 | Bailey et al. |
| 5,620,449 A | 4/1997 | Faccioli et al. |
| 5,624,440 A * | 4/1997 | Huebner .................. 606/59 |
| 5,630,814 A | 5/1997 | Ross, Jr. et al. |
| 5,658,283 A | 8/1997 | Huebner |
| 5,662,648 A | 9/1997 | Faccioli et al. |
| 5,662,649 A | 9/1997 | Huebner |
| 5,662,650 A | 9/1997 | Bailey et al. |
| 5,681,318 A | 10/1997 | Pennig et al. |
| 5,688,271 A | 11/1997 | Faccioli et al. |
| 5,690,633 A | 11/1997 | Taylor et al. |
| 5,707,370 A | 1/1998 | Berki et al. |
| 5,709,681 A | 1/1998 | Pennig |
| 5,728,096 A * | 3/1998 | Faccioli et al. .................. 606/54 |
| 5,743,898 A | 4/1998 | Bailey et al. |
| 5,755,646 A * | 5/1998 | Chu .................. 482/118 |
| 5,755,794 A | 5/1998 | Benson |
| 5,766,179 A | 6/1998 | Faccioli et al. |
| 5,769,851 A | 6/1998 | Veith |
| 5,788,695 A | 8/1998 | Richardson |
| 5,792,076 A | 8/1998 | Orsak et al. |
| 5,803,924 A | 9/1998 | Oni et al. |
| 5,814,050 A | 9/1998 | Benson |
| 5,827,282 A | 10/1998 | Pennig |
| 5,843,081 A | 12/1998 | Richardson |
| 5,881,878 A | 3/1999 | Faccioli et al. |
| 5,885,289 A | 3/1999 | Muller |
| 5,902,302 A | 5/1999 | Berki et al. |
| 5,921,985 A | 7/1999 | Ross, Jr. et al. |
| 5,941,877 A | 8/1999 | Viegas et al. |
| 5,951,556 A | 9/1999 | Faccioli et al. |
| 5,968,043 A | 10/1999 | Ross, Jr. et al. |
| 5,976,125 A | 11/1999 | Graham |
| 5,976,134 A | 11/1999 | Huebner |
| 5,976,136 A | 11/1999 | Bailey et al. |
| 6,010,501 A | 1/2000 | Raskin et al. |
| 6,015,413 A | 1/2000 | Faccioli et al. |
| 6,017,008 A * | 1/2000 | Farley .................. 248/229.21 |
| 6,024,745 A | 2/2000 | Faccioli et al. |
| 6,027,506 A | 2/2000 | Faccioli et al. |
| 6,036,691 A | 3/2000 | Richardson |
| 6,090,111 A * | 7/2000 | Nichols .................. 606/61 |
| 6,102,911 A | 8/2000 | Faccioli et al. |
| 6,106,556 A | 8/2000 | Demopulos et al. |
| 6,126,661 A | 10/2000 | Faccioli et al. |
| 6,143,012 A | 11/2000 | Gausepohl |
| 6,162,223 A | 12/2000 | Orsak et al. |
| 6,162,224 A | 12/2000 | Huebner |
| 6,171,307 B1 | 1/2001 | Orlich |
| 6,171,308 B1 | 1/2001 | Bailey et al. |
| 6,171,309 B1 | 1/2001 | Huebner |
| 6,217,577 B1 | 4/2001 | Hofmann |
| 6,235,029 B1 | 5/2001 | Faccioli et al. |
| 6,245,071 B1 | 6/2001 | Pierson |
| 6,277,118 B1 | 8/2001 | Grant et al. |
| 6,328,737 B1 | 12/2001 | Moorcroft et al. |
| 6,340,361 B1 | 1/2002 | Kraus et al. |
| 6,364,824 B1 | 4/2002 | Fitzsimmons |
| 6,409,729 B1 | 6/2002 | Martinelli et al. |
| 6,413,258 B1 | 7/2002 | Bernhardt, Jr. |
| 6,423,061 B1 | 7/2002 | Bryant |
| 6,428,540 B1 | 8/2002 | Claes et al. |
| 6,461,358 B1 | 10/2002 | Faccioli et al. |
| 6,482,206 B2 | 11/2002 | Schoenefeld |
| 6,491,694 B1 | 12/2002 | Orsak |
| 6,500,177 B1 | 12/2002 | Martinelli et al. |
| 6,508,817 B1 | 1/2003 | Pensler et al. |
| 6,565,564 B2 | 5/2003 | Hoffman et al. |
| 6,565,568 B1 | 5/2003 | Rogozinski |
| 6,605,088 B1 | 8/2003 | St. Onge et al. |
| 6,613,049 B2 | 9/2003 | Winquist et al. |
| 6,678,562 B1 | 1/2004 | Tepper et al. |
| 6,699,251 B1 | 3/2004 | Venturini |
| 6,709,433 B1 | 3/2004 | Schoenefeld |
| 6,722,368 B1 | 4/2004 | Shaikh |
| 6,749,611 B2 | 6/2004 | Venturini et al. |

| | | | |
|---|---|---|---|
| 6,770,075 B2 | 8/2004 | Howland | |
| 6,840,939 B2 | 1/2005 | Venturini et al. | 606/54 |
| 6,988,701 B1 | 1/2006 | Lin | |
| D518,174 S | 3/2006 | Venturini et al. | |
| 7,282,052 B2 | 10/2007 | Mullaney | |
| 2001/0034520 A1 | 10/2001 | Enayati | |
| 2002/0004659 A1 | 1/2002 | Boudard et al. | |
| 2002/0115998 A1 | 8/2002 | Schoenefeld | |
| 2002/0151892 A1 | 10/2002 | Walulik et al. | |
| 2003/0109879 A1 | 6/2003 | Orsak | |
| 2003/0139744 A1 | 7/2003 | Berki et al. | |
| 2006/0181080 A1* | 8/2006 | Guest | 285/322 |
| 2006/0229602 A1 | 10/2006 | Olsen | 606/54 |
| 2006/0229603 A1 | 10/2006 | Olsen | 606/54 |
| 2006/0229605 A1 | 10/2006 | Olsen | 606/54 |

FOREIGN PATENT DOCUMENTS

| | | |
|---|---|---|
| EP | 0011258 | 5/1980 |
| EP | 0 240 034 B1 | 10/1987 |
| EP | 0 261 252 | 3/1988 |
| EP | 0 314 021 A2 | 5/1989 |
| EP | 0 424 292 B1 | 4/1991 |
| EP | 0 216 563 B1 | 6/1991 |
| EP | 0 604 697 A1 | 7/1994 |
| EP | 0 685 206 A1 | 12/1995 |
| EP | 0 734 232 B1 | 2/1996 |
| EP | 0 717 986 A2 | 6/1996 |
| EP | 0 779 795 B1 | 6/1997 |
| EP | 0 609 409 B1 | 9/1998 |
| EP | 0 858 781 A3 | 5/1999 |
| FR | 2557933 | 7/1985 |
| NL | 8802463 | 5/1990 |
| WO | WO 89/09031 | 10/1989 |
| WO | WO 90/07305 | 7/1990 |
| WO | WO 90/11727 | 10/1990 |
| WO | WO 91/00111 | 8/1991 |
| WO | WO 94/02078 | 2/1994 |
| WO | WO 94/23662 | 10/1994 |
| WO | WO 95/04504 | 2/1995 |
| WO | WO 95/10240 | 4/1995 |
| WO | WO 95/16401 | 6/1995 |
| WO | WO 96/17557 | 6/1996 |
| WO | WO 96/35385 | 11/1996 |
| WO | WO 98/46156 | 10/1998 |
| WO | WO 98/51227 | 11/1998 |
| WO | WO 99/02097 | 1/1999 |
| WO | WO 99/04714 | 2/1999 |
| WO | WO 99/22661 | 5/1999 |
| WO | WO 99/30626 | 6/1999 |
| WO | WO 00/40163 | 7/2000 |

OTHER PUBLICATIONS

Orthofix Modulsystem—General Application Instructions. Jan. 1996, 28 pages.

Dr. Joachim Pfiel, *Unilateral Fixation Techniques in Limb Deformity Corrections*, 1994. 48 pages.

Dr. Dietmar Penning, *The Pennig Dynamic Wrist Fixator—Orthofix*. Mar. 25, 1992, 47 pages.

Orthofix Modulsystem, *These could drive you to distraction . . . callus distraction with the Limb Reconstruction System*, Jul. 1997, prior edition before May 21, 1997, 16 pages.

Professor M. Saleh, *Operative Technique*, Limb Reconstruction System, Orthofix Modulsystem, Mar. 1998, prior edition before May 21, 1997, 67 pages.

Non-final Office Action dated Oct. 31, 2006, for U.S. Appl. No. 11/083,547.

Final Office Action dated Jun. 22, 2007, for U.S. Appl. No. 11/083,547.

Interview Summary dated Oct. 9, 2007, for U.S. Appl. No. 11/083,547.

Advisory Action Before the Filing of an Appeal Brief dated Oct. 9, 2007, for U.S. Appl. No. 11/083,547.

Non-Final Office Action dated Jan. 9, 2008, for U.S. Appl. No. 11/083,547.

Interview Summary dated Mar. 6, 2008, for U.S. Appl. No. 11/083,547.

Interview Summary for U.S. Appl. No. 11/294,504.

Non-Final Office Action dated Mar. 17, 2008, for U.S. Appl. No. 11/294,504.

Interview Summary dated Oct. 26, 2007, for U.S. Appl. No. 11/083,566.

Final Office Action dated Jul. 20, 2007, for U.S. Appl. No. 11/083,566.

Non-Final Office Action dated Oct. 31, 2006, for U.S. Appl. No. 11/083,566.

Final Office Action dated May 30, 2008, 11 pages, for U.S. Appl. No. 11/083,547.

Notice of Allowance and Interview Summary dated Oct. 7, 2008, 9 pages, for U.S. Appl. No. 11/083,547.

Interview Summary dated Jul. 14, 2008, 2 pages, for U.S. Appl. No. 11/083,547.

Interview Summary dated Jul. 21, 2008, 4 pages, for U.S. Appl. No. 11/294,504.

Final Office Action dated Aug. 19, 2008, 14 pages, for U.S. Appl. No. 11/294,504.

Office Action dated May 13, 2008, 9 pages, for U.S. Appl. No. 11/083,566.

Interview Summary dated Jul. 14, 2008, 2 pages, for U.S. Appl. No. 11/083,566.

Final Office Action dated Nov. 14, 2008, 7 pages, for U.S. Appl. No. 11/083,566.

US 6,030,385, 02/2000, Faccioli et al. (withdrawn)

* cited by examiner

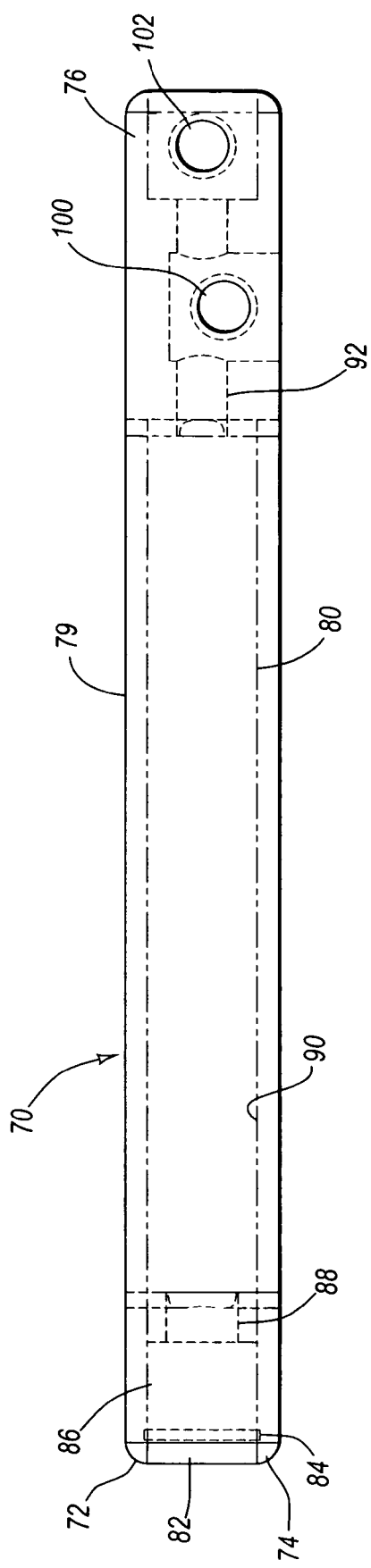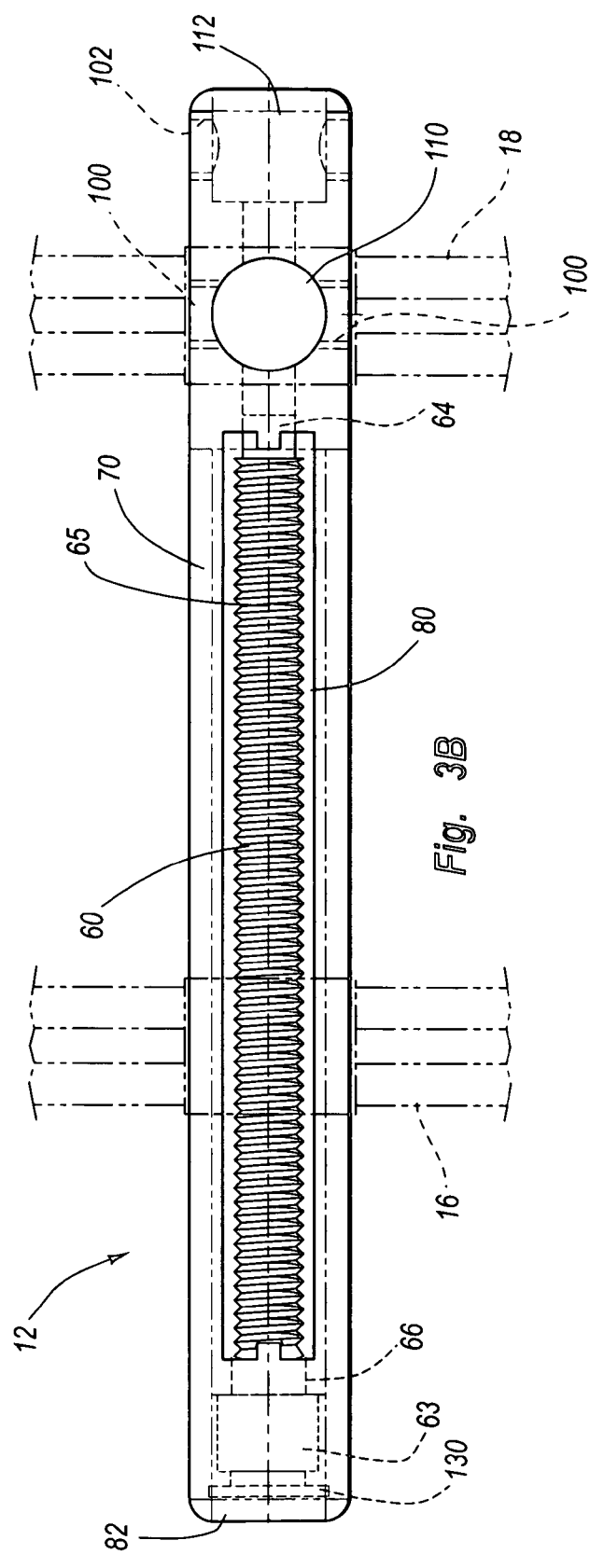
Fig. 3A
Fig. 3B

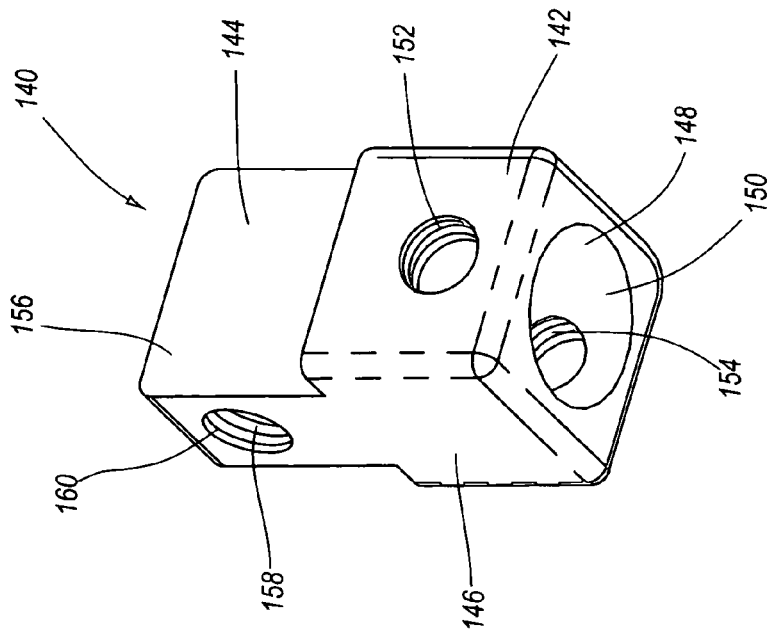
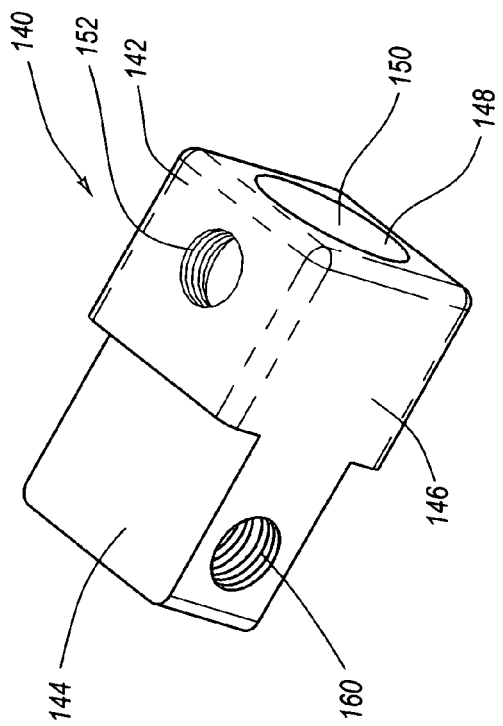
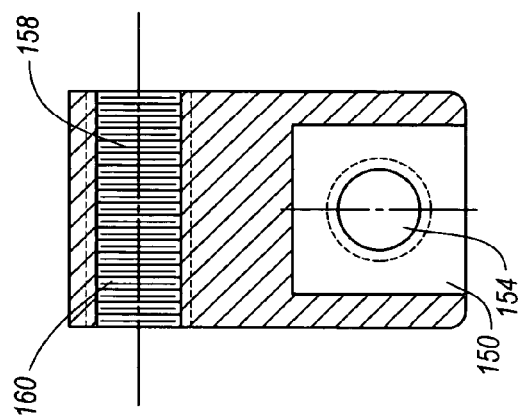

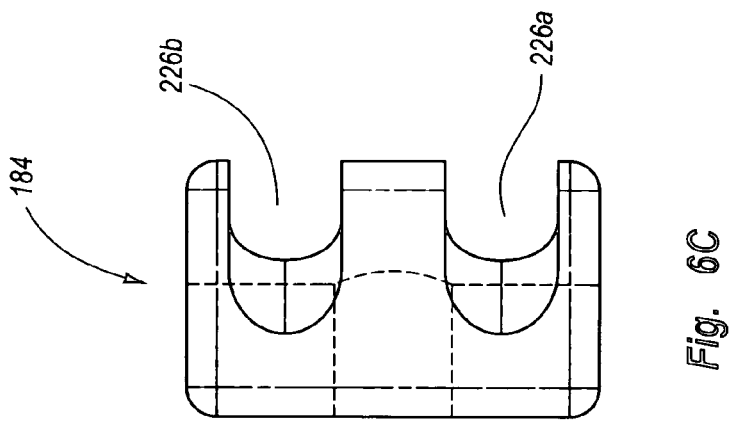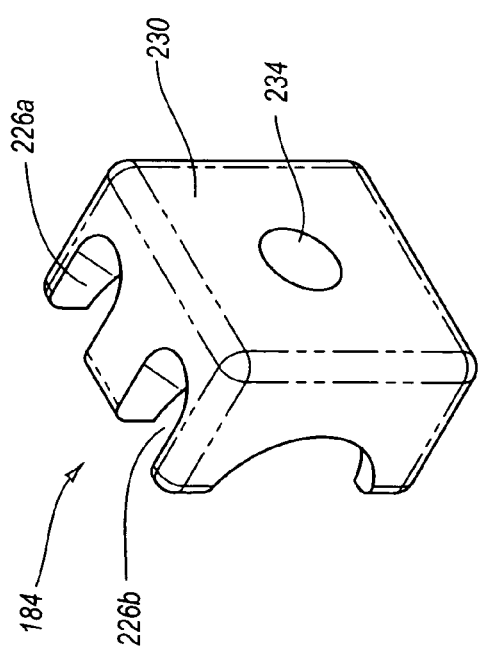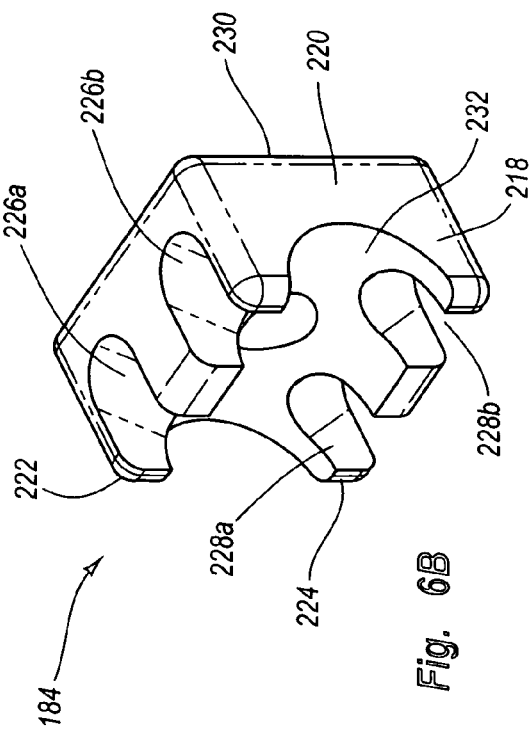

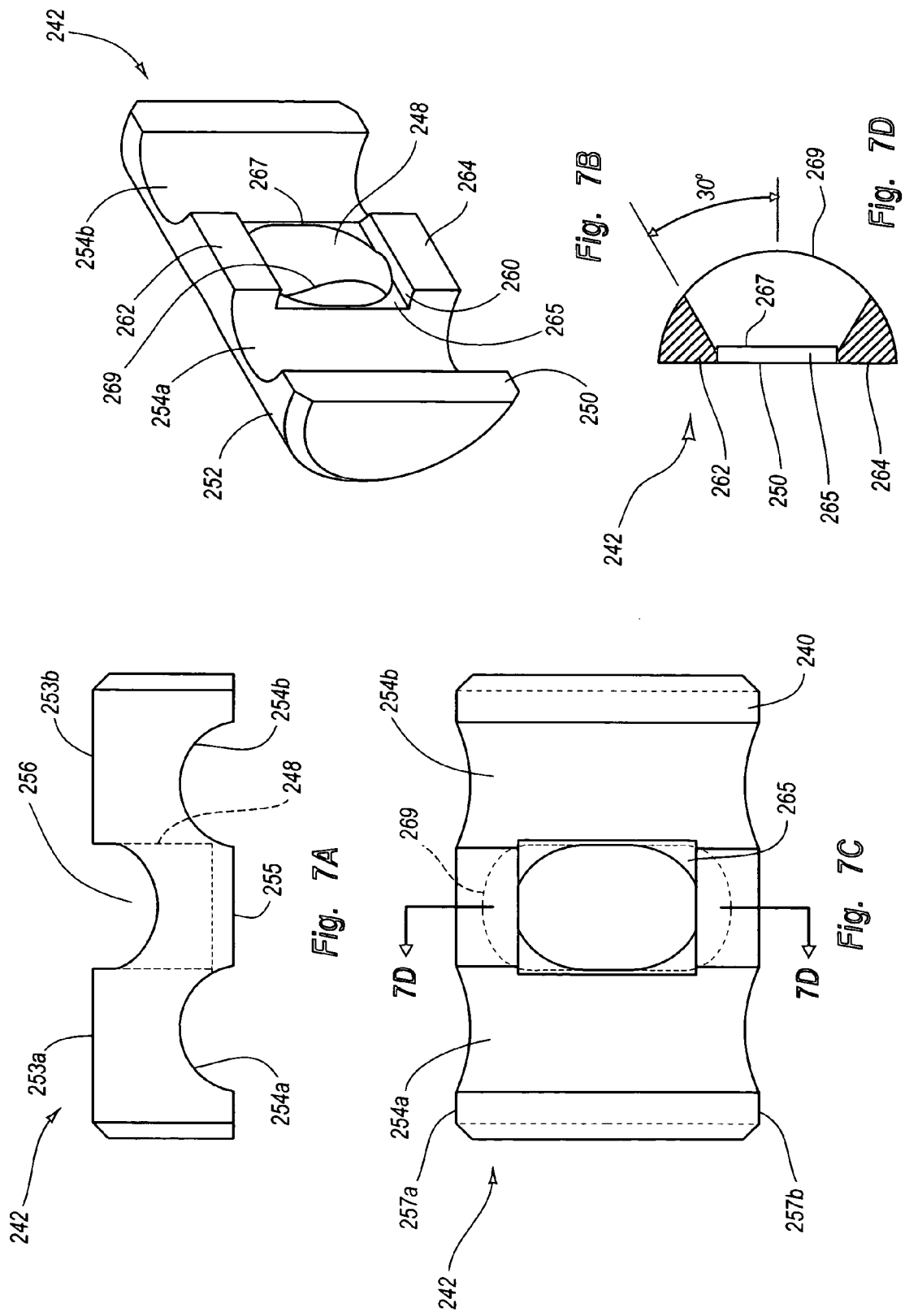

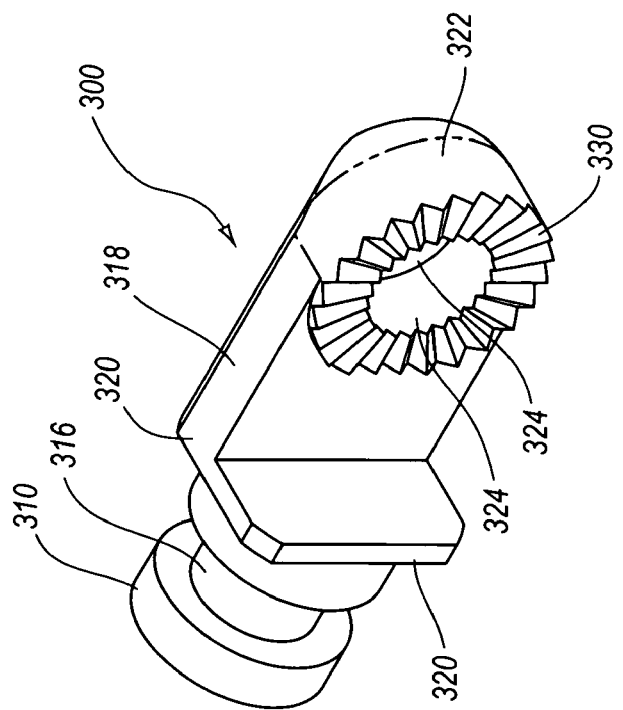
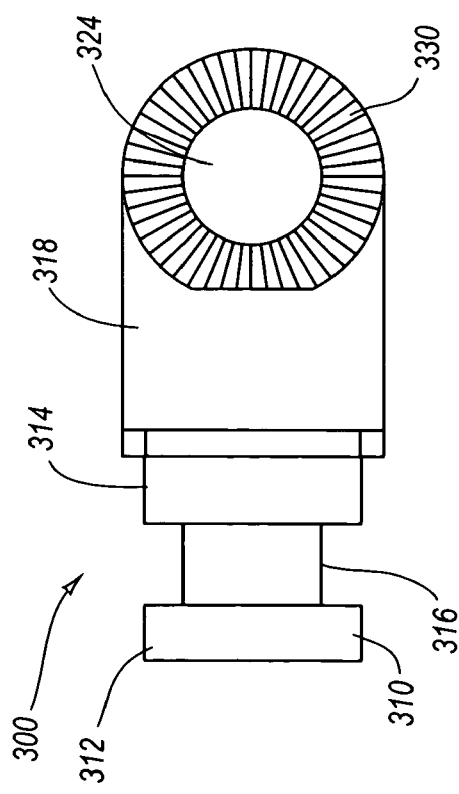
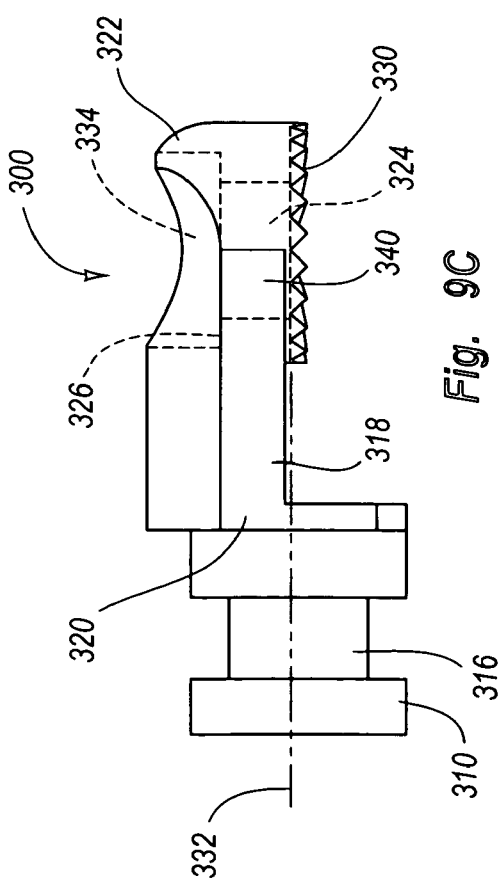

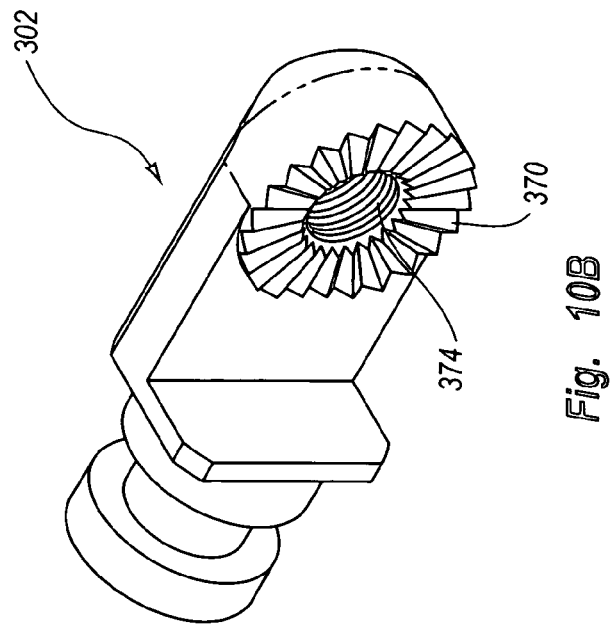
Fig. 10B
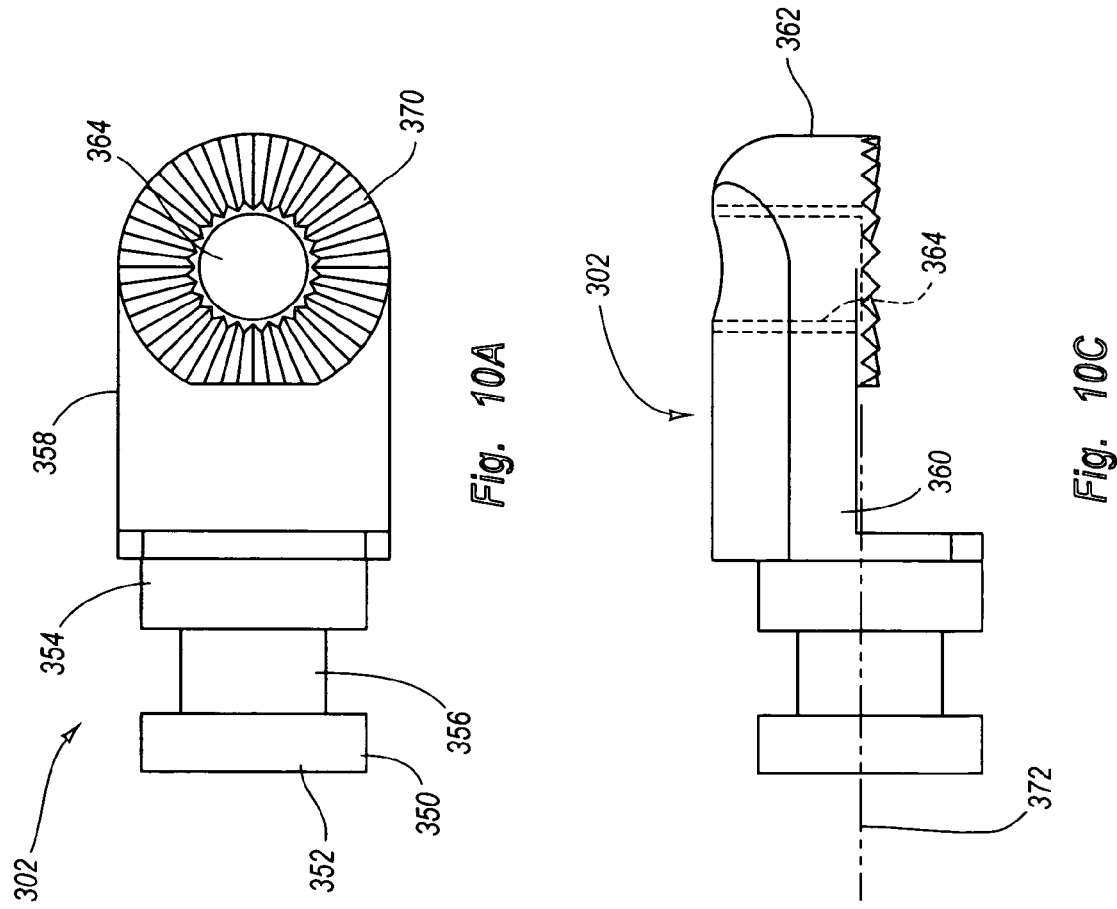
Fig. 10A
Fig. 10C

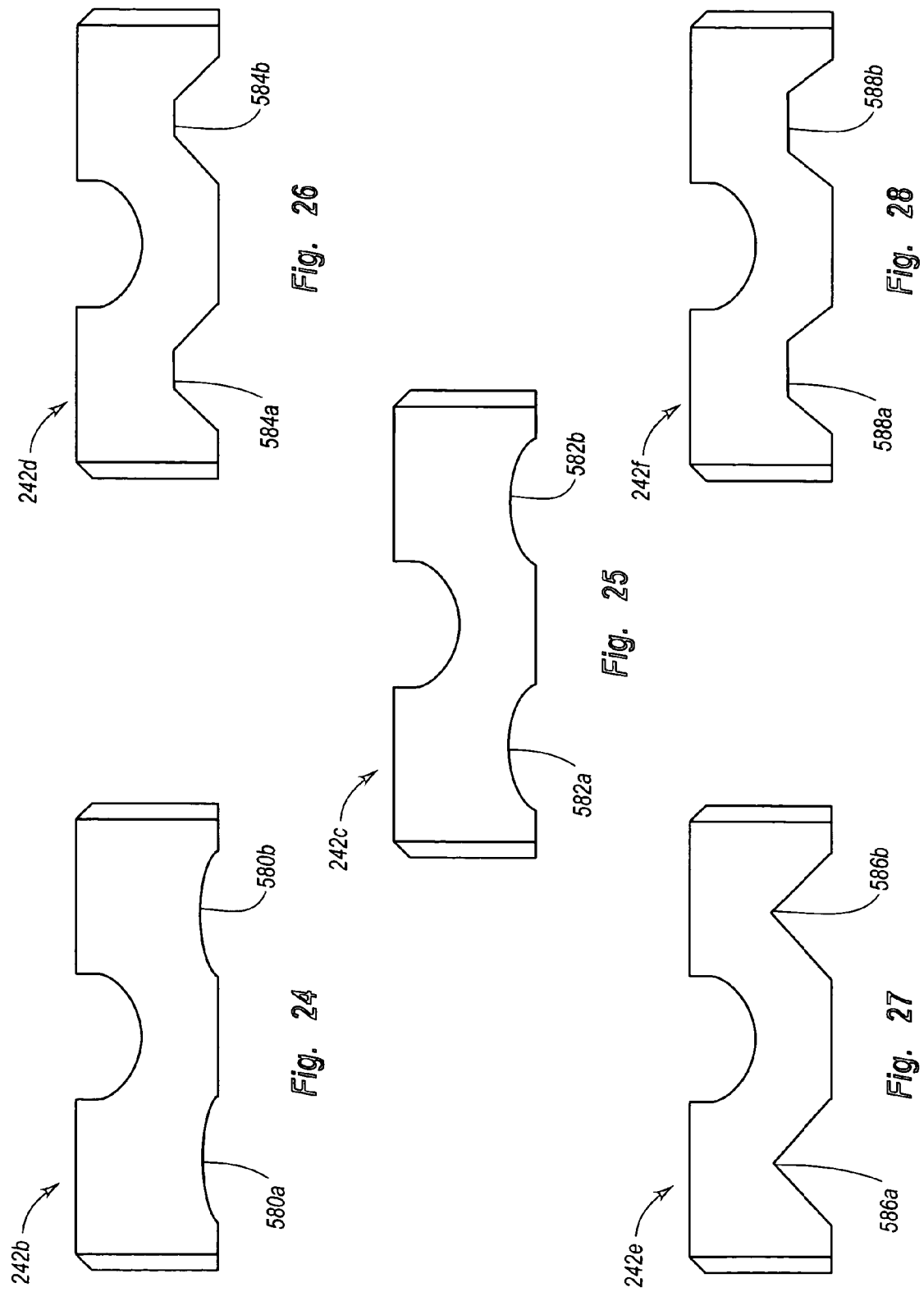

ADJUSTABLE SPLINT FOR OSTEOSYNTHESIS WITH MODULAR COMPONENTS

THE FIELD OF THE INVENTION

This patent application is in the field of adjustable splints for osteosynthesis. More specifically, this application relates to an adjustable splint device useful for treating the fracture of bones, e.g., ankle, wrist and facial bones.

BACKGROUND OF THE INVENTION

When fractured bones are properly splinted, they often are able to heal in an appropriate manner thereby simulating the shape and function of the previously uninjured, natural bone. Bone fixation devices are often employed in the treatment of fractures of small bones such as bones in the foot, hand or maxiofacial regions, but also with a variety of different bone types. Such fixation devices are often known as minisplint devices, particularly when used in treatment of the small bones.

Typical minisplint devices feature a longitudinal support body and a pair of clamps mounted on the longitudinal support body. A clamp can be moved along the body through the use of an adjustable lead screw extending through the support body. Bone screws that are transverse to the longitudinal body connect to the clamps and secure the minisplint to the bone. By adjusting the lead screw, the position of the clamps can be moved with respect to the longitudinal support, thereby adjusting the size and configuration of the splint and the location of the transverse bone screws.

One limitation to typical adjustable minisplint devices is that the clamp connected to the longitudinal support is only moveable in an axial, linear direction with respect to the longitudinal support. The bone screws are also limited in their orientation. This dynamic limits the practitioner's options when attempting to set one or more bones using such minisplint devices.

Another limitation with typical devices relates to the positioning of one longitudinal support with respect to another longitudinal support. Such positioning typically results in limited movement, again reducing treatment options.

Yet another limitation associated with previous minisplint devices is that the lead screw used to provide adjustment of the bone clamps is retained in the longitudinal support body through the use of complicated multi-part systems that require a number of different parts to be added to the device assembly.

Another disadvantage of typical devices is that the lead screw of the devices projects outwardly from the elongated body, thereby exposing the lead screw to being inadvertently turned.

BRIEF SUMMARY OF THE INVENTION

The adjustable splints of the present invention overcome the aforementioned disadvantages by providing a variety of different options for adjusting the locations and configurations of the splints. The adjustable mounts of the present invention can be moved to a variety of different locations with respect to the splint main body housings and the bone connectors can be rotated into a variety of positions within the mounts. Furthermore, the main bodies of the splint devices can be conveniently moved with respect to each other into a variety of different configurations and positions, thereby enabling them to be placed into a variety of different positions.

According to one embodiment, an adjustable splint for osteosynthesis comprises: (i) at least one main body; and (ii) first and second mounts coupled to the at least one main body, the first and second mounts adapted to couple to respective first and second bone connectors. One or more additional main bodies, e.g., two, three, four, five, etc., main bodies are also available, depending upon the required procedure.

In light of a unique slot design within the mounts, the bone connectors, e.g., bolts or screws may be moved from one position to another position (and a number of positions therebetween) within the mounts, thereby increasing the number of positions into which the splint may be placed.

To further increase the modularity and different positions of one embodiment of the splints of the present invention, at least one of the first and second mounts comprises: (i) an engaging member movably coupled to the at least one main body such that the engaging member is selectively moved from a first position to a second position with respect to the at least one main body; and (ii) a holding assembly movably coupled to the engaging member such that the position of the holding assembly can be adjusted with respect to the engaging member. The holding assembly can optionally be connected directly to one or more main bodies. The holding assemblies (whether connected directly to the mount or connected to an engaging member) can be rotated in a 360 degree range of motion, further increasing the number of positions available.

To enable the movement of the bone connectors with respect to the holding assembly, the holding assembly of one embodiment comprises: (i) a collar configured to grasp at least one bone connector; and (ii) a holder adapted to adjustably hold the collar therein.

The mounts may be connected in a variety of different manners to the main body or main bodies. For example, a lead screw can be positioned within a slot in a housing of the main body with a first end of the lead screw being rotatably coupled to a first end of the main body. The second end of the lead screw can be retained within the slot by a retaining member such as a split retaining ring positioned adjacent a terminal surface of the second end of the lead screw. The retaining ring retains the second end of the lead screw within the main body, thereby preventing the lead screw from extending out of the main body in an inconvenient fashion. The retaining ring can be mounted within a slot within the interior surface of the main body, for example.

In order to increase the different types of fractures that can be treated, the splint can have first, second, third, forth or additional main bodies, each having respective mounts and bone connectors coupled thereto. In such a configuration, in order to increase the range of motion of the splint, the first main body can be coupled to the second main body such that the first main body can rotate in at least two different planes with respect to the second main body.

In one embodiment, one main body can move in three or more different planes with respect to another main body. This can be achieved, for example, through the use of a universal joint connecting the first main body to the second main body.

In yet another embodiment, a three part joint is an employed, providing even further optional positions for the splints. In one such embodiment, three main bodies may be conveniently connected, each of which can be moved in at least two different planes with respect to each other, and the bone connectors of which can be moved in different planes, thereby enabling convenient fixation of complex multi-bone fractures.

The splints of the present invention are conveniently used for callous distraction, as bone reductive devices, and/or for dynamic compression of bones. The splints of the present invention may be conveniently used to treat fractures of the foot, hand, ankle, wrist, knee or any other bone or joint.

The splints of the present invention can also be conveniently installed in one piece or optionally in separate pieces, such as by first mounting a bone connector(s) with a mount coupled thereto onto a bone, then coupling a main body of the splint thereto. This may make installation in difficult places more convenient and is made possible because of the conveniently connectable components of the present invention.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 3A illustrate a top view of a housing of the main body of the splint of FIG. 1, while FIG. 3B illustrates a side view of the main body comprising the housing and the lead screw therein.

FIGS. 4A-4C illustrate front perspective, top perspective, and top cross sectional views, respectively, of an engaging member of the splint of FIG. 1.

FIGS. 6A-6C illustrate front perspective, rear perspective, and top views, respectively, of a front holder portion of the splint of FIG. 1.

FIGS. 7A-7D illustrate top, interior perspective, side perspective, and cross sectional views, respectively, of one part of a collar of the splint of FIG. 1, the opposing part of the collar having, in one embodiment, the same configuration.

FIGS. 9A-9C illustrate top, side perspective, and side views, respectively, of a first joint portion of the splint of FIG. 1.

FIGS. 10A-10C illustrate top, side perspective, and side views, respectively, of a second joint portion of the splint of FIG. 1, the first portion configured to adjustably mate with the teeth of second portion.

FIGS. 17A-8C illustrate top, side perspective, and side views, respectively, of a first outer joint portion of the splint of FIGS. 15 and 16.

FIGS. 18A-8C illustrate top, side perspective, and side views, respectively, of a second outer joint portion of the splint of FIGS. 15 and 16.

FIGS. 24-28 illustrate optional configurations of collar portions having optional groove configurations, illustrating that a variety of different collar grooves and bone connectors may be used in the present invention.

DETAILED DESCRIPTION OF THE PREFERRED EMBODIMENTS

Figure 1:
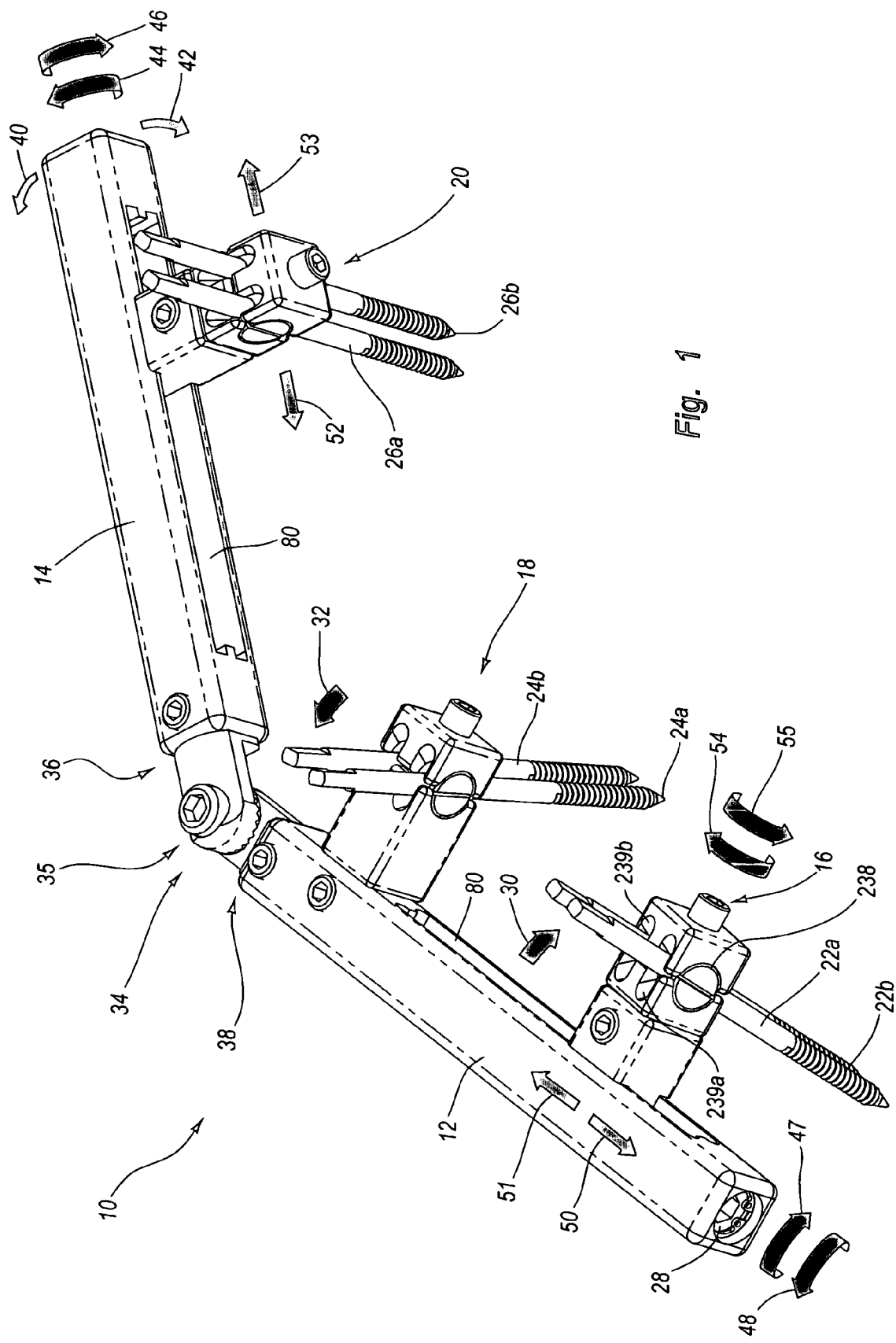
FIG. 1 illustrates an adjustable splint of the present invention, the arrows illustrating certain possible movement of the mounts, the bone connectors within the mounts, and the main bodies of the splint with respect to each other.

FIGS. 1-19 demonstrate examples of adjustable splints for osteosynthesis. FIG. 1 shows an adjustable splint 10 that is adjustable in more than one plane or axis, as illustrated by the arrows therein, thereby providing a variety of different, selectable splint configurations and treatment options for a practitioner. FIGS. 2-10 illustrate various individual components of splint 10, while FIGS. 11-14 illustrate various different positions in which the components of splint 10 can be moved to thereby provide adjustability and a variety of different optional configurations for the practitioner.

With reference now to FIG. 1, splint 10 has first and second main bodies 12, 14 to which respective first, second, and third mounts 16, 18, and 20 are coupled. Bone screws 22a-b, 24a-b, and 26a-b are coupled to respective mounts 16, 18, 20, and connect splint 10 to one or more selected bones during a bone splinting procedure. Each of these components may be selectively moved with respect to each other in a variety of different advantageous configurations, as illustrated by the arrows shown in FIG. 1, which will now be discussed in additional detail.

One advantage of adjustable splint 10 is that bone connectors, e.g., bone screws 22a-b, 24a-b, 26a-b are movably coupled to respective mounts 16, 18, 20 so as to selectively move from a first position within a respective mount 16, 18, 20 to a second position within a respective mount, as reflected by arrows 30, 32. More specifically, whereas screws 26a-b are in a perpendicular position with respect to main body 14, arrows 30, 32 illustrate that, in contrast, bone screws 22a-b, and 24a-b have been moved away from a position that is perpendicular to main body 12. Thus, as shown in FIG. 1, screws 22a-b, 24a-b, and 26a-b are selectively rotatable from a first position to a second position within a respective mount 16, 18 20. The screws 22a-b, 24a-b, and 26a-b rotate about an axis transverse to a longitudinal axis of screws 22a-b, 24a-b, and 26a-b. Thus, first mount 16 adjustably receives bone screws 22a-b therein, such that screws 22a-b are selectively fixed in one of: (i) a first position within the mount; and (ii) a second position within the mount and are selectively moved from the first position to the second position within the mount. This enables a practitioner to position the bone screws into a position that is most useful for attaching splint 10 to one or more bones.

Joint 34 connects main body 12 to main body 14. Joint 34 is comprised of multiple components that have selectively moveable connections at three interfaces 35, 36, 38. Movement of main body 12 with respect to main body 14 can occur at each of the first, second and third interfaces 35, 36, 38, respectively.

By moving at first interface 35, as shown in FIG. 1, joint 34 enables movement of second main body 14 with respect to first main body 12 in a first plane, as shown by arrows 40, 42. By moving at second interface 36, joint 34 enables movement of second main body 14 with respect to first main body 12 in a second plane, as shown by arrows 44, 46. Furthermore, by moving at third interface 38, joint 34 enables movement of second main body 14 with respect to first main body 12 in a third plane, as shown by arrows 47, 48.

FIG. 1 further illustrates that each of the mounts 16 and 20 are both slidable in the direction of arrows 50-51 and 52-53, respectively. Furthermore, FIG. 1 illustrates that mount 16 can be selectively rotated with respect to main body 12 in the direction of arrows 54 or 55. Mounts 18 and 20 can also be similarly rotated with respect to main bodies 12, 14. In the embodiment shown, mount 18 is not slidable with respect to main body 12, but rather is only rotatable with respect to main body 12.

Thus, FIG. 1 illustrates various optional, advantageous configurations of splint 10, namely: (i) bone connectors 22a-b, 24a-b, and 26a-b can be moved back and forth within respective mounts 16, 18, 20 (see arrows 30, 32); (ii) mounts 16, 18, and 20 can be selectively rotated with respect to main bodies 12, 14 (see arrows 54, 55); (iii) mounts 16, 20 can be selectively moved longitudinally within respective main bodies 12, 14 (see arrows 50, 51 and 52, 53); (iv) main body 14 can be moved in a horizontal plane with respect to main body 12 (see arrows 40, 42); (v) main body 14 can be twisted along one axis with respect to main body 12 (see arrows 44, 46); and (vi) main body 14 can be twisted, along another axis with respect to main body 12 (see arrows 47, 48).

Figure 2:
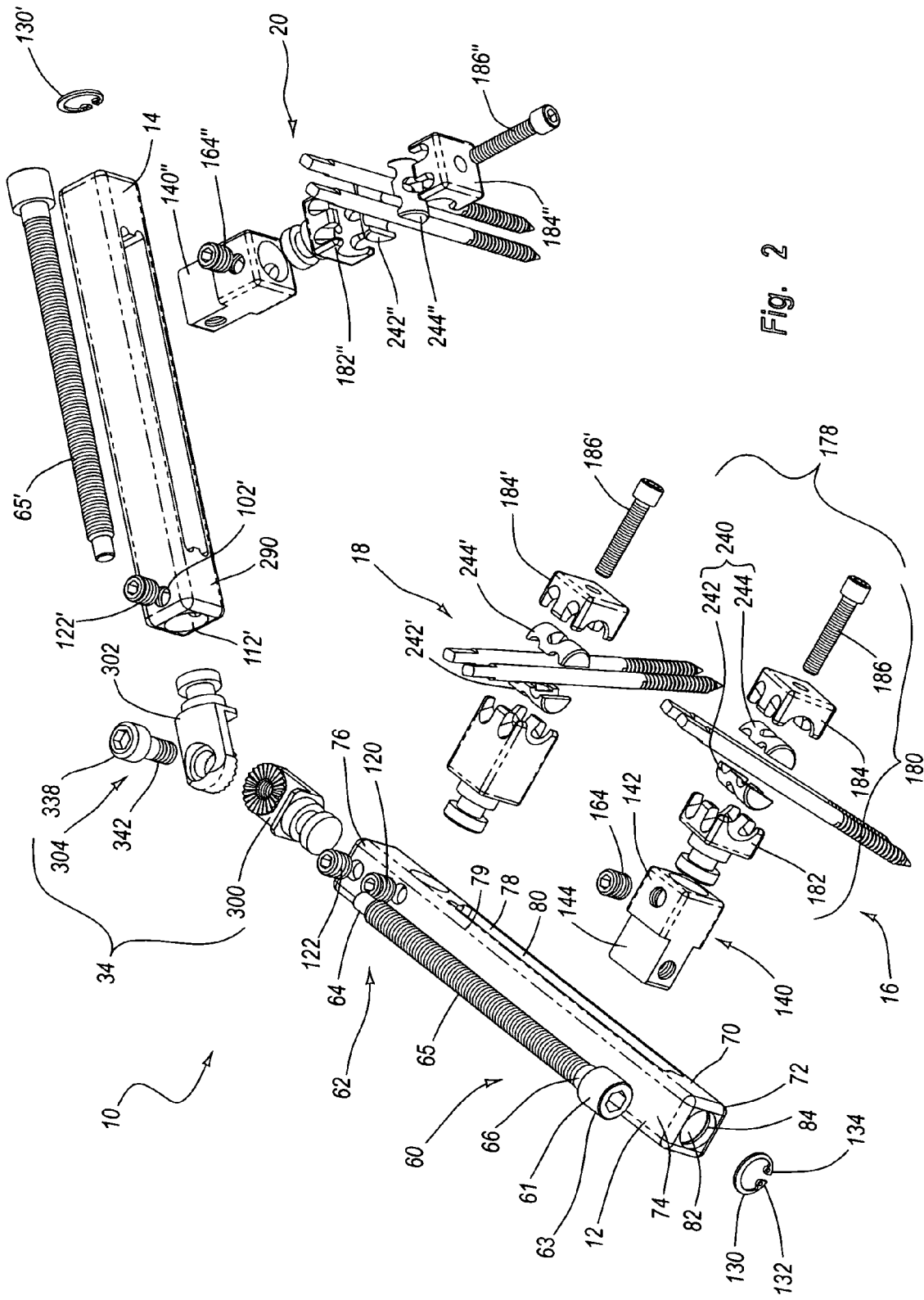
FIG. 2 illustrates an exploded perspective view of the splint of FIG. 1.

In order to describe the individual components of splint 10 in additional detail, an exploded view of splint 10 will now be discussed with reference to FIG. 2. FIG. 2 is an exploded, perspective view of the splint 10 shown in FIGS. 1 through 14. As shown in FIG. 2, main body 12 comprises a lead screw 60 and a housing 70 configured to receive the lead screw 60 therein. Lead screw 60 is configured to rotatably mount within housing 70 of main body 12.

Lead screw 60 comprises an elongate screw having a proximal end 61 and a distal end 62. A head 63 is located at the proximal end 61 while a smooth tip (i.e., non-threaded) 64 is located at the distal end 62. A threaded body 65 extends between the head 63 and the tip 64. Between head 63 and threaded body 65 is a smooth shoulder region 66. Head 63 is configured to receive a hex screwdriver tip therein in order to turn screw 60, although a variety of different shapes, configurations, and methods may be employed for turning the lead screw of the present invention.

With reference now to FIGS. 2 and 3A-3B, housing 70, in which lead screw 60 is movably coupled, will now be described in additional detail. Housing 70 comprises an elongate, hollow body 72 having a proximal end 74, a distal end 76, an interior surface 78, and an exterior surface 79. Interior surface 78 defines a slot 80 in which elongate screw 60 is movably mounted. More specifically, interior surface 78 defines a proximal aperture 82 at proximal end 74, an annular groove 84 adjacent proximal aperture 82, a head receiving chamber 86 (FIGS. 3A-B) adjacent groove 84, and an annular proximal internal shoulder 88 that is adjacent chamber 86. Annular groove 84 has a larger diameter than proximal aperture 82 and than chamber 86, and proximal shoulder 88 has a diameter that is smaller than chamber 86. From annular proximal shoulder 88, slot 80 widens into slot body chamber 90, then narrows again at a distal annular internal shoulder 92. Adjacent distal annular internal shoulder 92 is a first top aperture 100 extending through body 72 of housing 74. Adjacent first top aperture 100 is a second top aperture 102 extending through body 72 of housing 70.

With reference now to FIG. 3B, which is a side view of main body 12, lead screw 60 is shown mounted within housing. As illustrated, lead screw 60 is placed in housing 70 by extending lead screw through aperture 82 and inserting tip 64 of lead screw 60 into distal internal annular shoulder 92 (FIG. 3A), where tip 64 is retained within and rotates within shoulder 92. Threaded body 65 of lead screw 60 remains within slot body chamber 90 of housing 70 and shoulder region 66 of lead screw 60 is retained within and rotates within shoulder annular proximal internal shoulder 88. Head 63 of screw 60 is retained within and rotates within chamber 86.

As shown in FIGS. 2 and 3B, screw 60 is retained within slot 80 by a retaining member in the form of a bowed retaining ring 130 which is selectively placed within slot 84 after screw 60 is placed within slot 80, as shown in FIG. 3B. As illustrated in FIG. 2, retaining ring 130 of FIG. 2 has a split-ring shape. Ring 130 has a first end 132 and a second end 134, which form an incomplete circle. During assembly, ends 132, 134 of ring 130 can be compressed with respect to each other to thereby enable the retaining ring 130 to be pressed through aperture 82, then snapped fit into groove 84 during assembly, as reflected in FIG. 3b. Once lead screw 60 is placed within housing 70, retaining ring 130 is bent inward, then snapped into place in groove 84, thereby preventing lead screw 60 from exiting the interior surface of housing 70. This retains lead screw 60 within slot 80, as shown in FIG. 3b. In other words, ring 130 at the terminal end of screw 60 prevents screw 60 from extending proximally out of slot 80, while distal internal annual shoulder 92 prevents screw 60 from extending distally out of slot 80.

By rotating lead screw 60 within slot 80, mount 16, which is threadably coupled to lead screw 60, is selectively moved from one end of slot 80 to another end thereof, enabling a practitioner to achieve a configuration that is desirable for the setting of splint 10.

With continued reference to FIG. 3B, side hollow chamber 110 is shown. Side chamber 110 communicates with top aperture 100, which extends through body 72. Side chamber 110 may extend through the entire body 72 or may extend only partially therethrough. As illustrated in FIGS. 2-3B, a portion of mount 18 is inserted into side chamber 110, which has a circular cross section, and a screw 120 or other connector is inserted into top aperture 100, thereby retaining the cylindrical body portion of mount 18 within side chamber 110. By tightening the screw 120, mount 18 is firmly, immovably positioned at a desired position within chamber 110. By loosening screw 120, mount 18 is enabled to be rotated in a 360 degree range of motion in either direction within chamber 110. Screw 120 may then be tightened again to couple mount 18 to a fixed position again. Optionally, an additional screw may also be placed in the bottom portion of top aperture 100 to assist with retaining mount 18 therein.

Similarly, with continued reference to FIG. 3B, distal front hollow chamber 112 is shown. Distal front hollow chamber 112 has a circular cross section and is formed within body 12 and communicates with second top aperture 102, which extends through body 72. As illustrated in FIGS. 2-3B, a first joint portion 300 of joint 34 can be inserted into distal front chamber 112 and a screw 122 or other connector is inserted into distal front chamber 112, thereby retaining the cylindrical body of first joint portion 300 within distal front chamber 112. By tightening the screw 122, joint portion 300 is firmly, immovably positioned at a desired position within distal front hollow chamber 112. By loosening screw 122, joint portion 300 is enabled to be rotated in a 360 degree range of motion in either direction within chamber 112. An additional screw may also be placed in the bottom portion of second top aperture 102 to assist with retaining joint portion 300 therein.

Thus, aperture 100 and chamber 110 function to facilitate the adjustable connection of mount 18 to main body 12, while aperture 102 and chamber 112 function to facilitate the adjustable connection of joint portion 300 to main body 12.

Mount 16 will now be discussed in additional detail. As shown in FIG. 2, mount 16 comprises: (i) an engaging member 140; and (ii) holding assembly 178 coupled to engaging member 140. The holding assembly 178 is comprised of a holder 180 and a collar 240 coupled thereto.

Engaging member 140 is movably (i.e., threadably) coupled to lead screw 60 of main body 12 and is selectively moved from a first position to a second position, with respect to main body 12, through the movement of lead screw 60. By turning lead screw 70, mount 16 slides back and forth, along the direction of arrows 50, 51 (FIG. 1).

Engaging member 140 will now be described in additional detail, with reference to FIGS. 2 and 4A-4C. Engaging member 140 comprises a receiving member 142 and a sliding member 144, which, in the embodiment shown, extends integrally from receiving member 142.

Receiving member 142 has an exterior surface 146 and an interior surface 148, which defines a receiving chamber 150. Upper and lower apertures 152, 154, in receiving member 142, communicate with chamber 150. One or both apertures, 152, 154 are configured to receive set screw 164 or another connector threadably therein, so as to adjustably retain an additional portion of mount 16 therein. Although apertures 152, 154 are both threaded, it is possible to achieve the connection desired herein with only one aperture or with only one threaded aperture.

Extending from receiving member 142, e.g. in an integral fashion, is sliding member 144, which has an exterior surface 156 and an interior surface 158. The interior surface 158, defining a threaded slot 160, extends from one end of the sliding member 144 to the other. Thus, interior surface 158 defines a threaded slot 160 through which threaded body 65 of lead screw 60 threadably moves, thereby advancing sliding member 144 in a desired direction when sliding member 144 is placed within slot 80 of housing 70.

Engaging member 140, is also configured to adjustably connect to holding assembly 178, which holds bone connectors 22a-b. As mentioned, holding assembly 178 is comprised of a holder 180 and a collar 240 coupled thereto. Holder 180 holds collar 240 therein and comprises multiple components, which will now be described with continued reference to FIG. 2 and additionally to FIGS. 5a through 7D.

Holder 180 comprises a rear holder portion 182, a front holder portion 184, and a holding assembly connector, such as a bolt 186, which extends through front portion 184 and into rear portion 182 and couples rear portion 182 to front portion 184 to form holder 180. The rear and front holder portions 182, 184 and bolt 186 that collectively form holder 180 are adapted to adjustably hold the two-piece collar 240. Bolt 186 thus extends through collar 240 to maintain collar 240 in a fixed position with respect to holder 180.

Figure 5B:
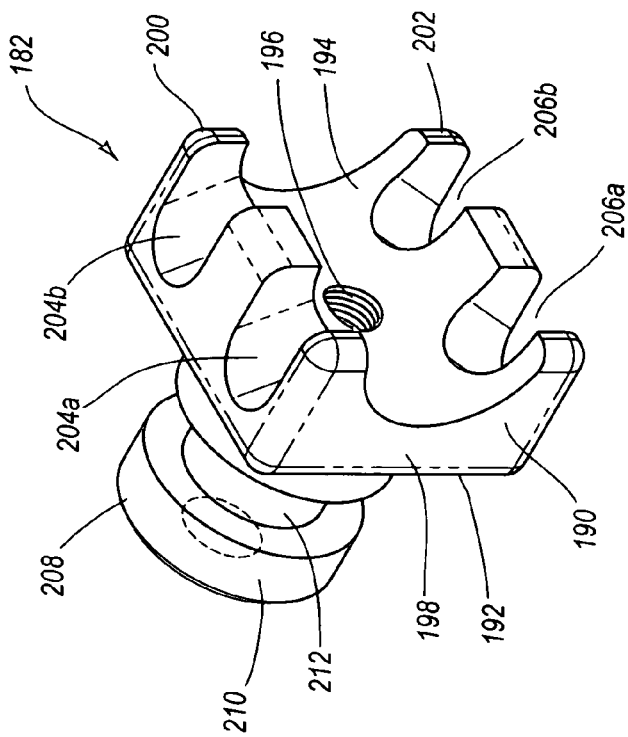
FIGS. 5A-5C illustrate top perspective, side perspective, and top cross sectional views, respectively, of a rear holder portion of the splint of FIG. 1.
Figure 5A:
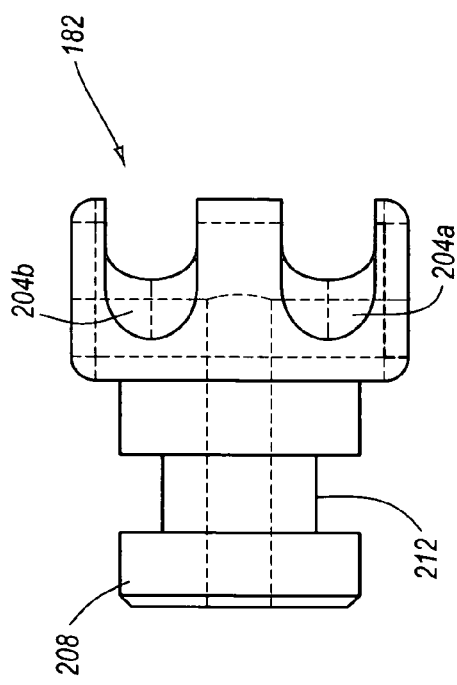
Figure 5C:
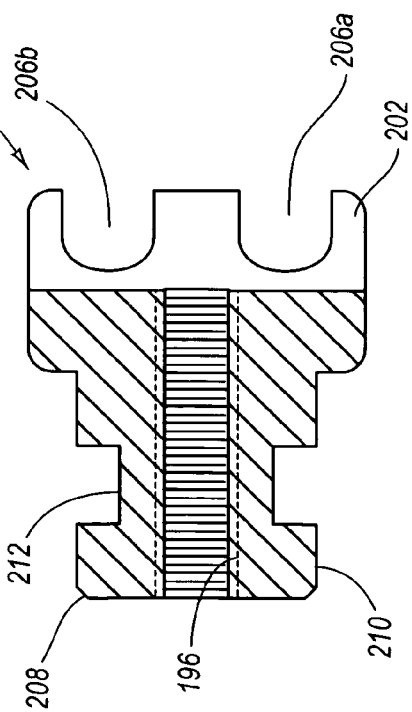

Rear holder portion, 182, will now be described in additional detail with reference to FIGS. 5a through 5c. Rear holder portion 182 comprises a U-shaped member 190, having an exterior surface 192 and a U-shaped interior surface 194. The interior surface 194 has a threaded slot 196 therein. The U-shaped member has a central portion 198 and upper and lower leg members 200 and 202 extending therefrom, each of the leg members having corresponding groove portions 204a, 204b, and 206a, 206b, therein, respectively. In FIG. 5B, groove portion 204a is positioned above groove portion 206a, while groove portion 204b is positioned above groove portion 206b.

Coupled to the U-shaped member 190 (e.g. integrally extending from U-shaped member 190) is a cylindrical member 208, comprising a cylindrical body 210 having an annular groove 212 therein. The slot 196 of U-shaped member 190 continues through cylindrical member 208, as shown in FIG. 5C.

Cylindrical body 210 is received in mating relationship within chamber 150 and enables convenient 360 rotation with respect to the main body 12. Cylindrical body 210 is configured to be positioned and received within receiving chamber 150 of engaging member 140, and is selectively coupled thereto through the use of screw 164 or another connector. Screw 164 selectively extends through aperture 152 (FIG. 4A) and into annular groove 212 (FIGS. 5A-C), thereby retaining cylindrical body 210 in a desired position within receiving chamber 150 of engaging member 140. In order to rotate holder 180 in either direction in a 360 degree range of motion, set screw 164 is loosened, and mount 16 is then rotated in the direction of arrow 54 or 55 (FIG. 1), then the set screw 164 is tightened again, thereby securing the position of holder 180 with respect to engaging member 140.

As mentioned above, in order to form holder 180, rear holder member 182 is combined through the use of a connecting member e.g. screw 186, to front holder member 184, which will now be discussed with reference to FIG. 2 and FIGS. 6a through 6c. Similar to rear member 182, front holder member 184 comprises a U-shaped member 218 having a central portion 220 and upper and lower legs, 222, 224, extending therefrom, each leg 222, 224 having a pair of corresponding groove portions 226a, 226b and 228a, 228b therein, respectively. In FIG. 6B, groove portion 226a is positioned above groove portion 228a, while groove portion 226b is positioned above groove portion 228b.

Front holder member 184 has an exterior surface 230 and a U-shaped interior surface 232. A slot 234 extends from the exterior surface 230 to the interior surface 232, such that bolt 186 may be extended during assembly through front member 184 of holder 180 until reaching and threading into rear holder member 182 to thereby form holder 180.

As reflected in FIGS. 1 and 2, when front holder member 184 and rear holder member 182 are placed adjacent to each other, such that the U-shaped interior surfaces 232 and 194 are adjacent to each other in a symmetrical, complimentary fashion, a substantially circular cavity 238 (FIG. 1) is formed there between. Furthermore, the respective groove portions of rear holder member 182 and front holder member 184 combine to form elongate upper holder slots 239*a-b* (FIG. 1) and corresponding elongate lower holder slots which are formed below corresponding upper holder slots 239*a-b*. Upper holder slot 239*a* is formed from the combination of groove 204*a* of rear holder member 182 with groove 226*b* of front holder member 184. Upper holder slot 239*b* is formed from the combination of groove 204*b* of rear holder member 182 with groove 226*a* of front holder member 184. The lower holder slots are similarly formed from the combination of grooves 206*a*, 206*b* of rear holder member 182 with corresponding grooves 228*b*, 228*a* of front holder member 184. Each of the elongate upper holder slots 239*a-b* and the elongate lower holder slots extend from the exterior surface to the interior surface and communicate with the cavity 238.

The upper slots 239*a-b* and lower slots of holder 180 enable screws 22*a-b* to move in a range of motion, which in one embodiment is approximately 40 degrees in each direction, for a total 80 degree range of motion. Two-part collar 240, which holds screws 22*a-b* within holder 180 and rotates within holder 180 in order to achieve such range of motion, will now be discussed in additional detail.

As shown further shown in FIGS. 1, 2, and 7A through 7D, two-part collar 240 is a substantially cylindrically-shaped collar that fits within the substantially cylindrical-shaped cavity 238 that is formed between front holder member 184 and rear holder member 182. Collar 240 retains bone screws 22*a-b* within holder 180, i.e., rotatably within cavity 238 and also allows replacements of screws 22*a-b* so that differently sized and shaped screws 22*a-b* may be employed in splint 10.

As shown, collar 240 comprises a rear collar member 242 and a front collar member 244. Rear collar member 242 will now be discussed in additional detail, keeping in mind that in the embodiment of FIGS. 1 and 2, the front collar member 244 has the same or substantially similar configuration as that of rear collar member 242.

Rear collar member 242 comprises a substantially half-cylindrically shaped member, having an interior face surface 250 and an exterior rounded surface 252. Collar member 242 further has a first end portion 253*a* and a second end portion 253*b* and a central portion 255 therebetween. First and second opposing, substantially half-cylindrically-shaped parallel elongate grooves 254*a-b* are made in respective opposing ends 253*a*, 253*b* of the interior face surface 250, each extending from a top 255*a* of interior surface 250 to a bottom 255*b* thereof. Grooves 254*a-b* are perpendicular to the axis of rear collar member 242.

A third substantially half-cylindrically-shaped groove 256 is made in the exterior rounded surface 252 in the central portion 255 of collar member 242. Also located in central portion 255 of interior surface 250 between grooves 254*a*, 254*b* is a notched portion 260 formed between an upper central face surface 262 and a lower central face surface 264. Notched portion 260 has an inner surface 265 of interior surface 250. Inner surface 265 of interior surface 250 has an interior rim 267. Exterior rounded portion 252 has an exterior rim 269. An oval shaped slot 248 extends from interior rim 267 to exterior rim 269. Slot 248 thus extends from rim 267 of interior surface 250 to rim 269 of the exterior surface 252 in the central portion 255 of rear collar member 242.

Slot 248 forms a passageway through which bolt 186 extends during assembly to properly orient collar 240 within holder 180. As shown, as slot 248 extends from interior surface 250 to exterior rounded surface 252, the size of the oval shaped slot 248 increases. Specifically, oval shaped slot 248 increases in size (i.e., top to bottom) as slot 248 extends from inner surface 265 to exterior rounded surface 252. This increase in size is an upward and downward flaring of slot 248 as it extends towards the exterior surface 252 and also reflects an increase in cavitation in the exterior rounded surface, as opposed to the inner surface 265. In one embodiment, slot 248 flares at an angle of approximately 30 degrees with respect to a longitudinal axis of slot 248, as shown in FIG. 7D.

This flaring and increased cavitation in the exterior rounded surface 252 enables each collar member 242, 244 to be rotated dramatically with respect to bolt 186, thereby enabling collar 240 to be rotated about bolt 186 when bolt 186 is extended through collar 240 and holder 180 once splint 10 is assembled.

Thus, the oval shaped aperture 267 is smaller in height than aperture 269, and as slot 248 extends from aperture 267 to aperture 269, the size of slot 248 increases. This increase in height enables the exterior rounded surface 252 of collar member 242 to be moved with respect to bolt 186 without significantly moving the interior surface 250 thereof.

As shown in FIG. 7D, in one embodiment, the angle of inclination of the upper surface (and in the embodiment shown, the lower surface) of slot 248 is about 30 degrees with respect to the longitudinal axis of slot 248. As a result, in one embodiment, collar 240 and the connectors retained therein can be moved about 40 degrees in each direction, for a total range of motion of about 80 degrees.

As illustrated in FIGS. 1-2, grooves 254*a-b* correspond to similar or identical grooves of front collar member 244. Two-part collar 240 conveniently receives and retains screws 22*a-b* between corresponding grooves in collar members 242, 244. The collar 240 with screws 22*a-b* therein is placed within cavity 238 of holder 180, thereby enabling screws 22*a-b* to be retained within respective grooves 239*a*, 239*b* of holder 180 and to move into a desired orientation therein. Thus, in summary, screws 22*a-b* are held firmly between grooves 254*a-b* of collar member 242 and mating grooves of collar member 244. The screws move within the upper and lower slots of holder 180. Each collar member 242, 244 of the two-piece collar 240 has a slot 248 therethrough that is configured to receive a holding assembly connector 186 therethrough.

FIGS. 1 and 2 thus illustrate the combination of components that form mount 16. During assembly a user decides which screws 22*a-b* to use for a particular procedure, keeping in mind that a variety of different diameter screws 22*a-b* may be placed in collar 240. Upon selecting the desired screws (or optionally a single screw), collar members 242-244 are mounted onto opposing sides of the screw(s) to form a screw/collar 240 assembly.

Rear and front holder members 182, 184 are then mounted onto respective opposing sides of the screw/collar 240 assembly such that screws 22*a-b* can be moved back and forth within upper holder slots 239*a*, 239*b* and lower holder slots. Attachment bolt 186 is then extended through holder member 184, collar member 244, collar member 242, and secured within holder member 182 such that holder members 182 and 184 are securely fixed to each other with collar 240 maintained tightly therebetween. When it is desired to adjust the position of collar 240, and hence screws 22*a-b*, attachment bolt 186 is loosened and collar 240 is rotated to a desired position. Attachment bolt 186 is then tightened, retaining collar 240 in the new desired position with respect to holder 180.

The holding assembly 178, which comprises collar 240 and holder 180 can be connected to engaging member 140 by mounting cylindrical body 210 of rear holding member 182 within receiving chamber 150 of engaging member 140 and by threading a screw 164 or other connector into aperture 152 and into annular groove 212 of cylindrical body 210, thereby adjustably retaining cylindrical body 210 within receiving chamber 150 of engaging member 140.

Hence, bone connectors 22a-b are housed within a substantially cylindrically shaped collar 240 that selectively rotates within a two-part holder 180 when bolt 186 is loosened. As mentioned, in one embodiment, collar 240 can rotate about 40 degrees in either direction, such that collar 240 can effectively rotate about 80 degrees. This approximately 80 degree range of motion enables bone connectors 22a-b to be placed into a variety of different positions.

As further illustrated in FIG. 2, second mount 18 is also coupled to first main body 12. In the embodiment shown, mount 18 is not slidably coupled to first main body 12, but is rotatable in a 360 degree range of motion with respect to first main body 12, such that it can be adjusted into a desired position with respect thereto. Mount 18 will now be discussed in additional detail with respect to FIG. 8.

Figure 8:
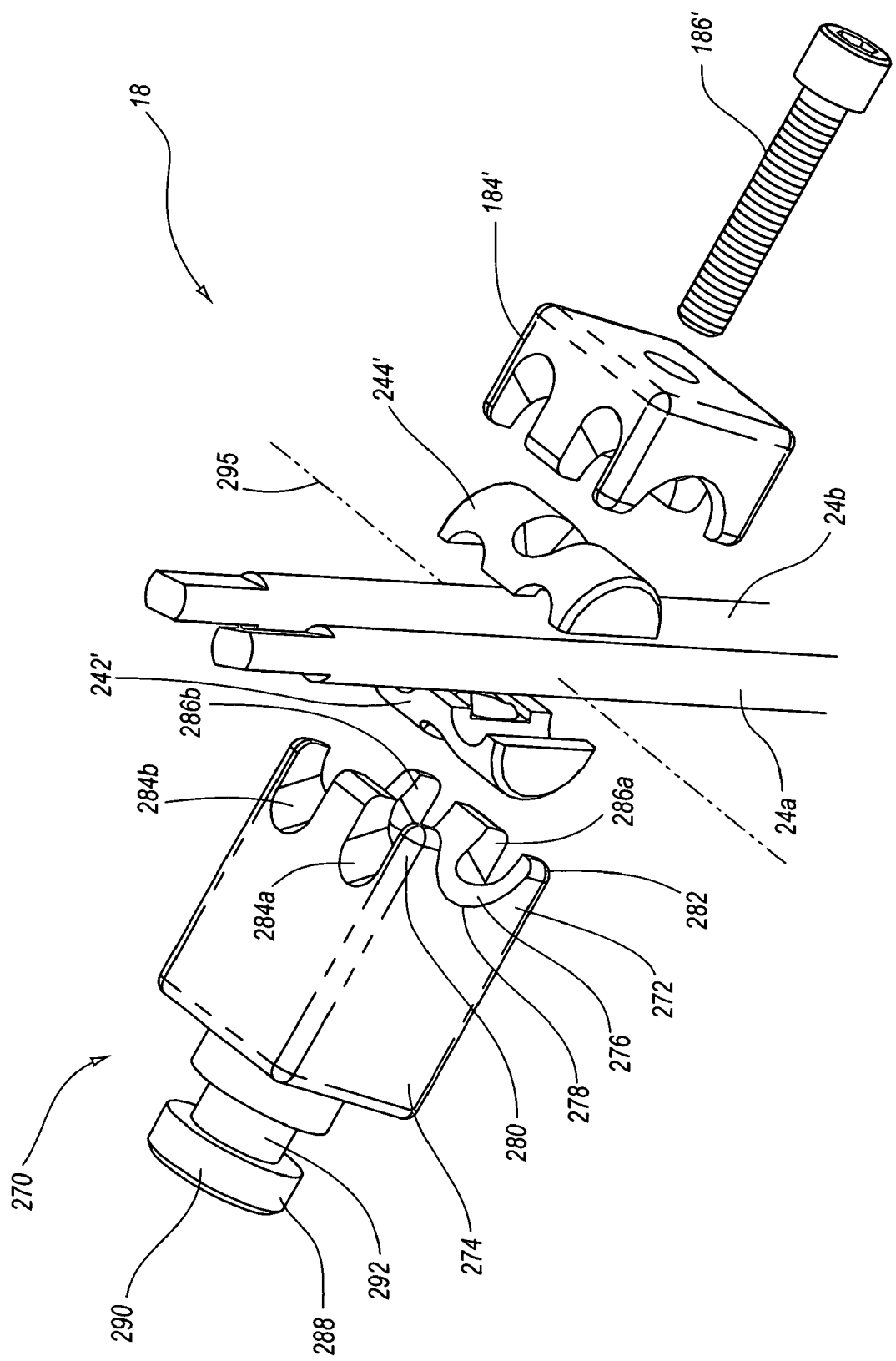
FIG. 8 illustrates a mount assembly comprising another rear holder portion of the splint of FIG. 1 that has a longer body than the rear holder portion of FIGS. 5A-C, but is otherwise, in one embodiment, similar or identical to the rear holder portion of FIGS. 5A-C. A perspective view of the arrangement of the second mount components, including the collar and holder portions, with respect to each other is shown.

In the embodiment of FIG. 8, the components of mount 18 are the same or similar to those of mount 16, except that mount 18 does not have the engaging member 140 of mount 16. Thus, in one embodiment, the collar members 242', 244' of mount 18 are identical to respective collar members 242, 244 of mount 16 and the front holder member 184' and bolt 186' are identical to member 184 and bolt 186 of mount 16. However, in the embodiment shown, the rear holder member 270 of mount 18 shown in FIG. 8 is similar, but not identical to rear holder member 182 of mount 16, since the size of a portion of the rear holder member 270 is longer than that of member 182.

Similar to rear holder portion 182 of mount 16, rear holder portion 270 of mount 18 comprises a U-shaped member 272, having an exterior surface 274 and a U-shaped interior surface 276, which has a threaded slot therein (not shown), which is configured to threadably receive bolt 186'. The U-shaped member 272 has a central portion 278 and upper and lower leg members 280 and 282 extending therefrom, each of the leg members having corresponding groove portions 284a, 284b, and 286a, 286b, therein, respectively.

Coupled to the U-shaped member 272 (e.g. integrally extending from U-shaped member 190) is a cylindrical member 288, comprising a cylindrical body 290 having an annular groove 292 therein. Cylindrical body 290 is received in mating relationship within chamber 110 of main body 12 and enables convenient 360 degree rotation with respect to the main body 12.

The exterior surface 274 of rear member 270 is longer than that of the exterior surface of member 182, such that rear member 270 extends to main body without the use of an engaging member, such as member 140. Optionally, however, an engaging member may be employed in another embodiment.

FIG. 8 also demonstrates an axis 295 that is transverse to the longitudinal axis of bone screw 24a. Bone screw 24a rotates about axis 295 when bone screw 24a is moved within mount 18. Axis 295 is also parallel to a longitudinal axis of main body 12. Thus, FIG. 8 illustrates that bone screw 24a is selectively movable about an axis 295 that is parallel to a longitudinal axis of main body 12.

FIGS. 1, 2 and 8 illustrate that the holder 180 substantially encloses the collar 240, thereby protecting the collar 240 and bone connectors received therein from the environment and providing an efficient, non-cumbersome mechanism which has relatively few moving parts. These figures illustrate that holder 180 encloses a first end of the collective collar 240 (corresponding to collar member end 253a in FIG. 7), a second end of the collar 240 (corresponding to collar portion end 253b in FIG. 7), and a central portion of the collar 240 located between the first and second ends of the collar 240.

With reference again to FIG. 2, main body 14 is also substantially similar to main body 12, although a variety of different designs may be employed. Main body 14 comprises a housing 290 that is similar to housing 70 of main body 12, but does not feature the side aperture 102 of housing 70. In another embodiment, however, one, two, three or more such apertures may be present for receiving additional holding assemblies. Lead screw 65' may operate similarly or identical to lead screw 65, for example and is retained in housing 290 through the use of bowed retaining ring 130'.

The mount 20 connected to main body 14 may have components that are similar or identical to the components of mount 16 connected to main body 12. Thus, mount 20 comprises: (i) an engaging member 140" configured to selective move along screw 65'; and (ii) a holding assembly coupled to engaging member 140". The holding assembly comprises (i) a holder comprising a rear holder member 182", a front holder member 184" and a bolt 186" configured to connect the front holder to the rear member; and (ii) a collar comprising first and second collar members 242", 244" configured to grasp first and second screws 26a-b therebetween and to selectively rotate within members 182", 184" when loosened and to be fixed therebetween when tightened. The holding assembly is connected to the engaging member 140" through the use of one or more screws 164" for example. These components and relationships of mount 20 may be identical to the description of the components of mount 16 described above, or may be similar thereto, for example.

The joint 34 (FIG. 1) connecting main body 12 to main body 14 will now be described in additional detail with reference to FIGS. 1, 2 and 9A-10C. Joint 34 comprises a first joint member 300, a second joint member 302, and a connector, such as a bolt 304 or screw selectively connecting first joint member 300 to second joint member 302. Joint 34 conveniently acts as a universal joint, allowing movement in a variety of different directions.

As illustrated in FIGS. 2 and 9A-C, first joint member 300 comprises: (i) a cylindrical body 310 having a first end 312 and a second end 314 and an annular groove 316 therebetween; (ii) an extension member 318 extending from the cylindrical body 310, the extension member 318 having a first end 320 that is coupled to the second end 314 of the cylindrical body 310 and a second end 322 having an aperture 324 therein; and (iii) a circular array of teeth 330 on the second end 322 of member 318 extending concentrically about the aperture 324 such that the aperture extends through the teeth 330 and the second end 322 of extension member 318. Cylindrical body 310 is received in mating relationship within chamber 112 and enables convenient 360 degree rotation with respect to the main body 12 selectively connected thereto. Extension member 318 extends away from cylindrical body 310 such that the longitudinal axis of extension member 318 is aligned with the longitudinal axis 332 (e.g., parallel to, or along the same axis) of cylindrical body 310. Hence, teeth 330 are oriented transversely to the longitudinal axis 332 of cylindrical body 310.

Aperture 324 defines a chamber 334 having an internal ridge 326 on which the head 338 of bolt 304 rests when joint 34 is assembled. Chamber 334 further comprises a passageway 340 through which the body 342 of bolt 304 extends during assembly.

Thus, in summary, first joint member 300 has (i) a cylindrical body 310 at a first end of joint member 300 which adjustably couples to first main body 12; and (ii) an aperture 324 at a second end of first joint member 300 about which teeth 330 extend.

As illustrated in FIGS. 2 and 10A-C, second joint member 302 comprises: (i) a cylindrical body 350 having a first end 352 and a second end 354 and an annular groove 356 therebetween; (ii) an extension member 358 extending from the cylindrical body 350, the extension member 358 having a first end 360 that is coupled to the second end 354 of the cylindrical body 350 and a second end 362 having an aperture 364 therein; and (iii) a circular array of teeth 370 on the second end 362 of member 358 extending concentrically about the aperture 364, such that the aperture extends through the teeth 370 and the second end 362 of extension member 358. Cylindrical body 350 is received in mating relationship within chamber 112' and enables convenient 360 degree rotation with respect to the main body 14 selectively connected thereto. Extension member 358 extends away from cylindrical body 350 such that the longitudinal axis of extension member 358 is aligned with the longitudinal axis 372 (e.g., parallel to, or along the same axis) of cylindrical body 350. Hence, teeth 370 are oriented transversely to the longitudinal axis 372 of cylindrical body 350. Aperture 364 defines a threaded passageway 374 through which the body 342 of bolt 304 extends during assembly. Second joint member 302 thus has (i) a cylindrical body 350 at a first end of joint member 302 which adjustably couples to second main body 14; and (ii) an aperture 364 at a second end of second joint member 302 about which teeth 370 extend.

Thus, during assembly, as illustrated in FIG. 2, the corresponding teeth of each joint member 300, 302 are aligned and placed adjacent each other in mating relationship, such that the apertures 324, 364 extending through each joint member 300, 302 are aligned so as to receive bolt 304 within both apertures 324, 364. Bolt 304 is then extended through aperture 324 of first joint member 300 and threaded into aperture 364 of second joint member 302, thereby retaining joint members 300, 302 in a fixed, aligned position with respect to each other. Upon desiring to adjust the orientation of one joint member with respect to the other, bolt 304 is loosened and the joint members 302, 304 are realigned (i.e., the teeth are realigned with respect to each other), after which the bolt 304 is replaced and tightened.

Each of the cylindrical bodies 310, 350 of respective joint members 300, 302 are selectively, adjustably connected to respective main bodies 12, 14 through the use of respective connectors such as screws 122, 122' which are extended through respective top apertures 102, 102' when respective cylindrical bodies 310, 350 are placed in a desired position within respective front chambers 112, 112'. Upper and lower screws may be employed in each main body, or optionally only a single screw 122, 122' may be employed for each such connection.

Figure 11:
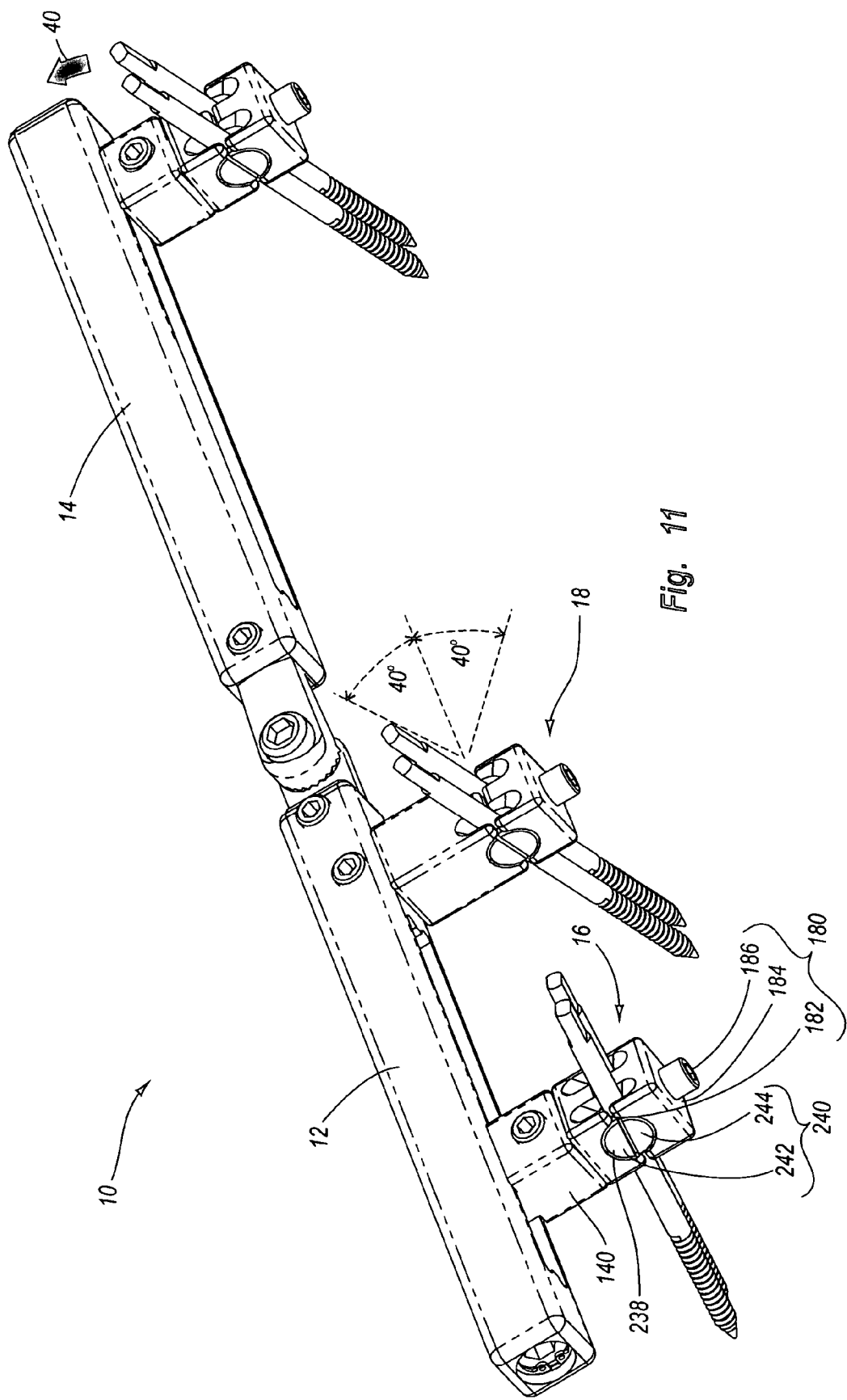
FIG. 11 illustrates the adjustable splint of FIG. 1 with the second main body moved away from the first main body in a horizontal plane in the direction of the arrow shown.

Thus, in order to adjust the orientation of main body 14 with respect to main body 12, bolt 304 (FIG. 2) may be loosened and main body 14 may be moved in the direction of arrow 40, as shown in FIG. 11. Also, as mentioned above, in one embodiment, collar 240 and the connectors retained therein can be moved about 40 degrees in each direction. Such a range of motion is illustrated at mount 18 in FIG. 11, for a total range of motion, in one embodiment, of about 80 degrees for the collars described herein, such as collar 240, etc.

Figure 12:
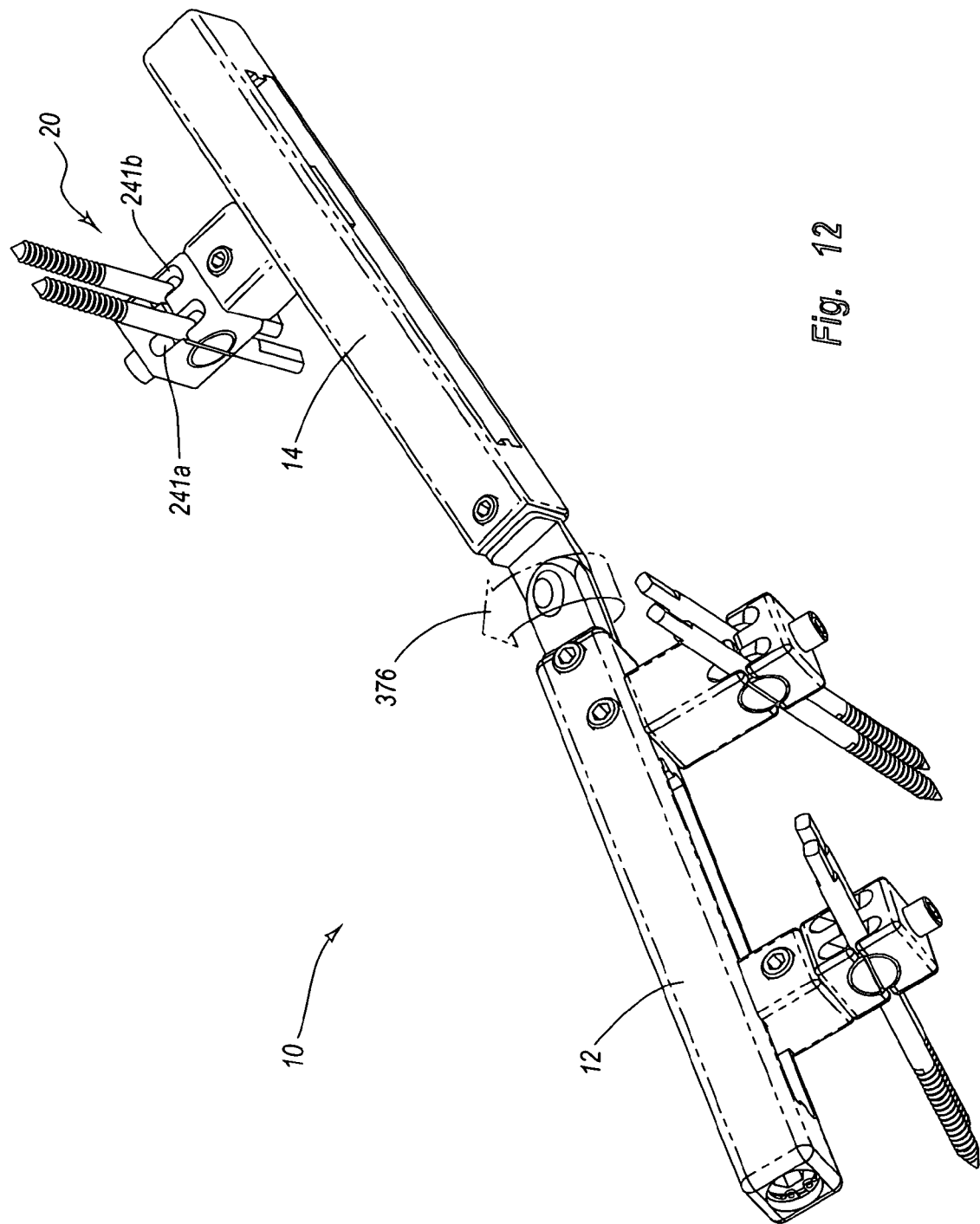
FIG. 12 illustrates the adjustable splint of FIG. 1 wherein the second main body has been moved 180 degrees with respect to the first main body.
Figure 13:
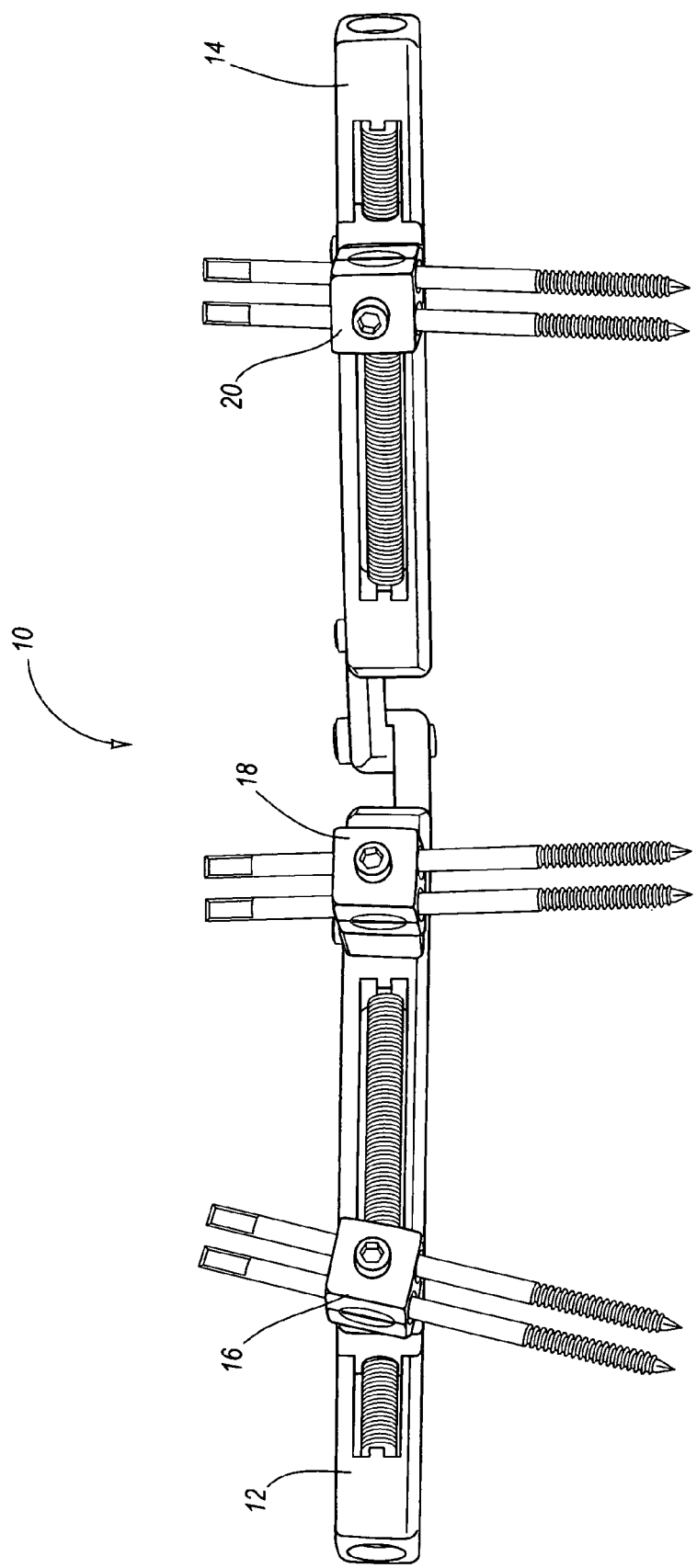
FIG. 13 illustrates a front view of the adjustable splint of FIG. 1.
Figure 14:
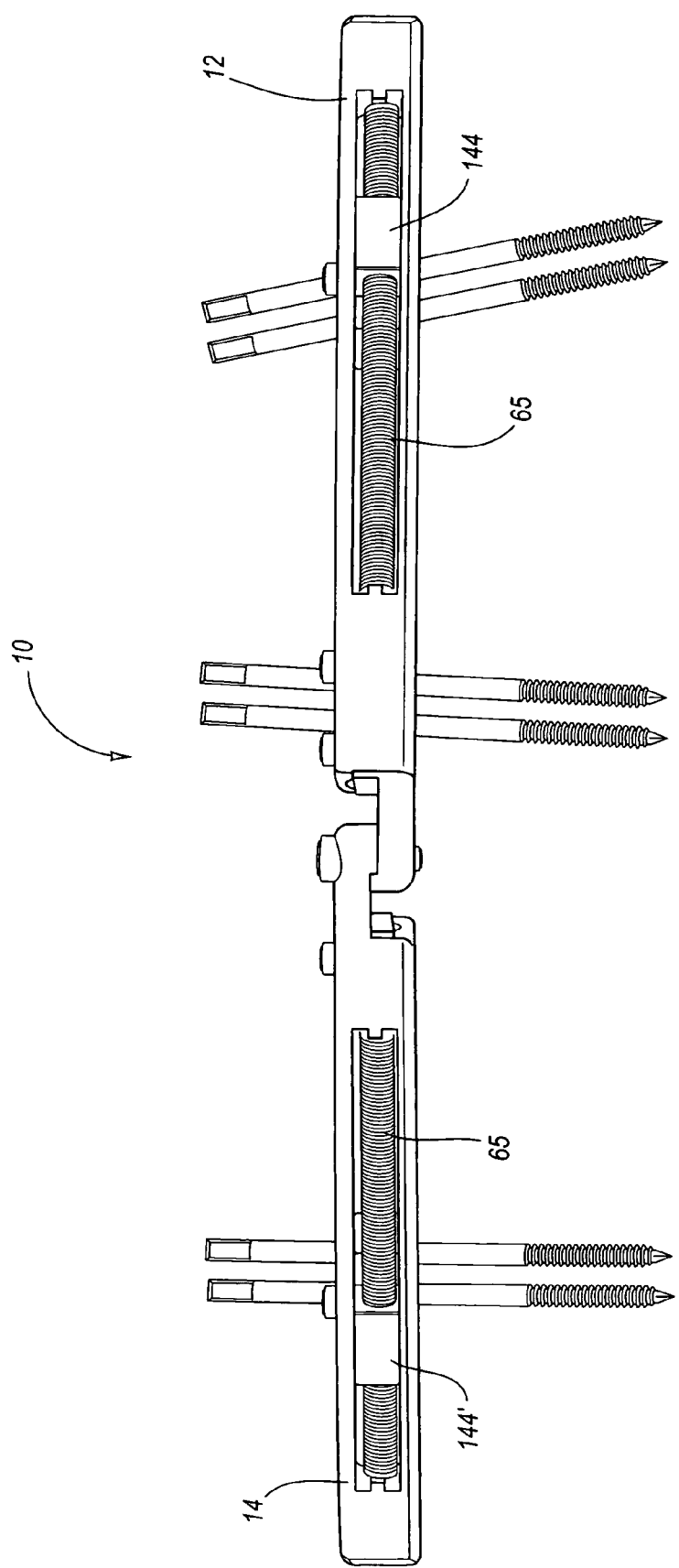
FIG. 14 illustrates a rear view of the adjustable splint of FIG. 1.

Optionally, screw 122 of FIG. 2 (and/or a lower screw in main body 12) may be loosened and main body 14 may be twisted in the direction of arrow 376, as shown in FIG. 12 (see also arrow 48 of FIG. 1) or in the direction of arrow 47 of FIG. 1. FIG. 12, which shows the bottom side of main body 14, also shows the lower holder slots 241a, 241b of mount 20. Mount 16 may have identical or similar lower holder slots beneath upper holder slots 239a-b for movement of bone connectors 22a-b therein. FIG. 13 shows a front view of splint 10, while FIG. 14 shows a rear view thereof.

Through the use of joint members 300, 302, it is possible for each respective main body 12, 14 coupled thereto to achieve 360 degrees of rotation about a respective joint member 300, 302, i.e., about the cylindrical body thereof. Also, the use of interlocking teeth and the interlocking ridges and surfaces thereof enable the use of long lever arms and decrease the amount of potential displacement between joint members 300, 302.

In summary, as shown in FIG. 1, splint 10 is a highly adjustable and modular splint 10 that can be used in a variety of different positions in order to treat a variety of different fractures or other breaks. Movement can occur in a variety of different planes and axes and from a variety of different positions to another. Thus, splint 10 is an example of a splint that has multi-faceted adjustability in a variety of different directions and positions. Adjustment can be achieved through sliding, rotating, twisting, back and forth movement, and in a variety of different manners.

As shown in FIG. 2, both holder 180 and collar 240 are two-part assemblies. However, in another embodiment, the holder and collar, are each a single member rather than being two-part assemblies.

One embodiment of the present invention features at least one main body to which at least one adjustable mount is movably coupled. In yet another embodiment, two, three, four, five, etc. main bodies are employed.

Thus, although FIG. 1 illustrates first and second main bodies 10, connected to each other, in another embodiment, only a single main body, e.g., main body 10 is employed, such as by connecting mount 16 to one portion of a bone, while connecting mount 18 to another portion of the bone.

Figure 15:
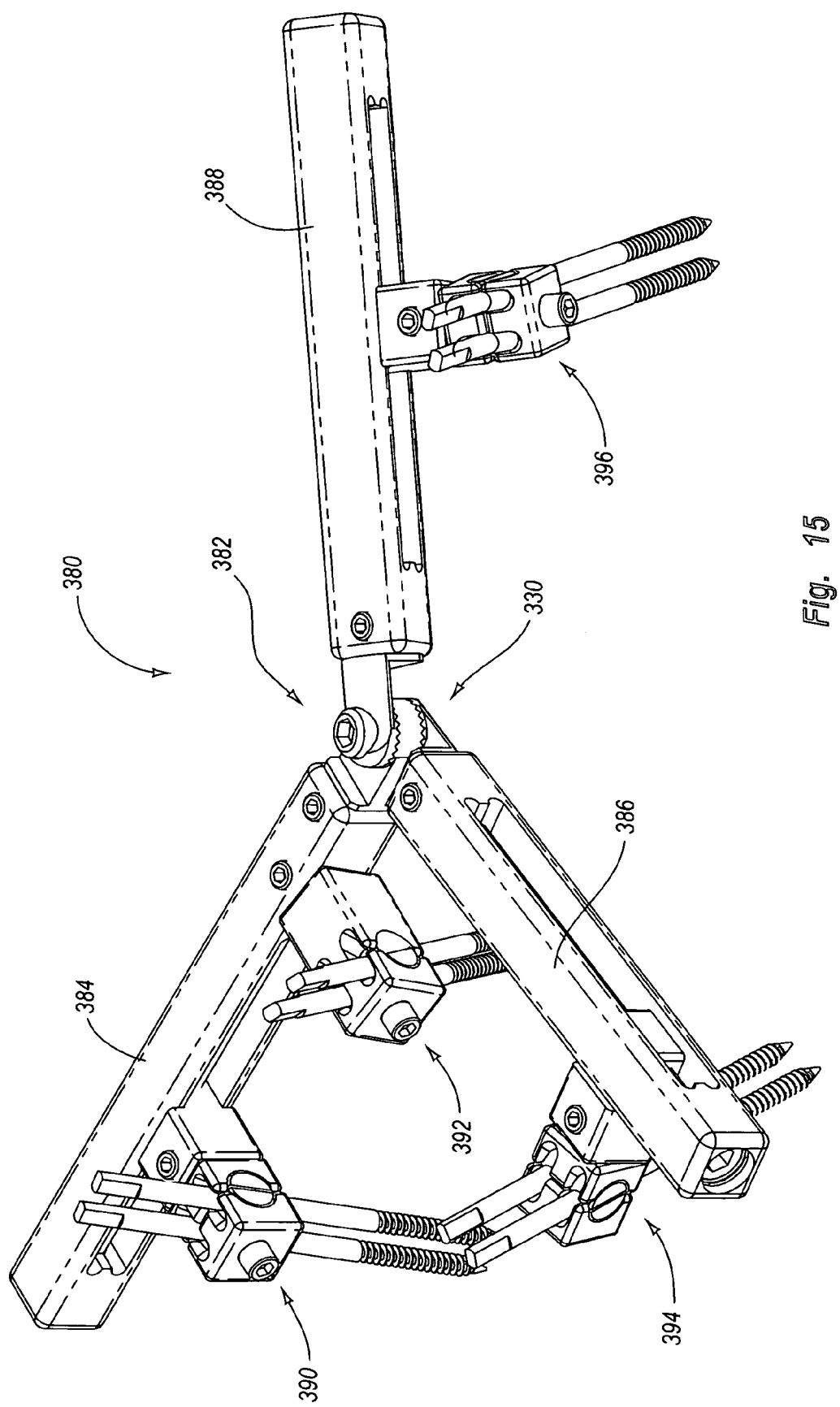
FIG. 15 illustrates another splint of the present invention having three main bodies connected by a three part joint.

FIG. 15 illustrates yet another embodiment of a splint 380 of the present invention that is available through the use of a three-part joint 382. Specifically, three part joint 382 enables splint 380 to have first, second and third main bodies 384, 386, 388 having respective mounts 390-392, 394 and 396 thereon. By having three main bodies, additional bone surfaces may be contacted for treating complicated fractures and brakes, such as in the ankle, hand, and facial areas. In one embodiment, the main bodies 384, 386, and 388 and mounts 390-392, 394 and 396 are identical or similar to the main bodies and mounts described previously herein.

Figure 16:
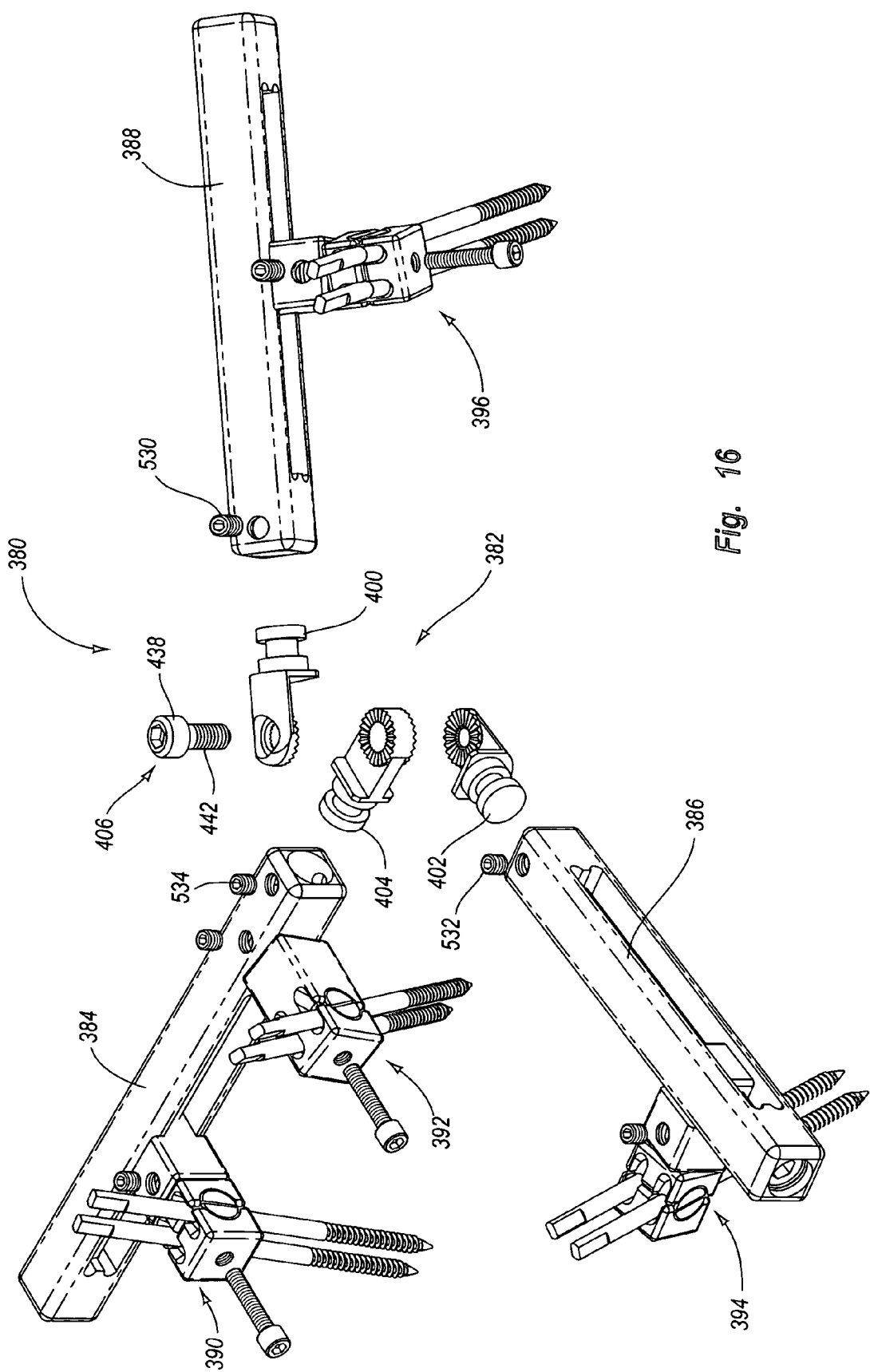
FIG. 16 illustrates an exploded perspective view of the three main body splint of FIG. 15.

With reference now to FIGS. 15 and 16, three part joint 382 comprises upper joint member 400, lower joint member 402, and middle joint member 404, which is configured to be sandwiched between upper and lower joint members 400, 402. Joint members 400, 402, 404 function substantially similarly to the joint members discussed above with reference to splint 10. However, by having three joint members, additional main bodies may be employed.

Figure 17B:
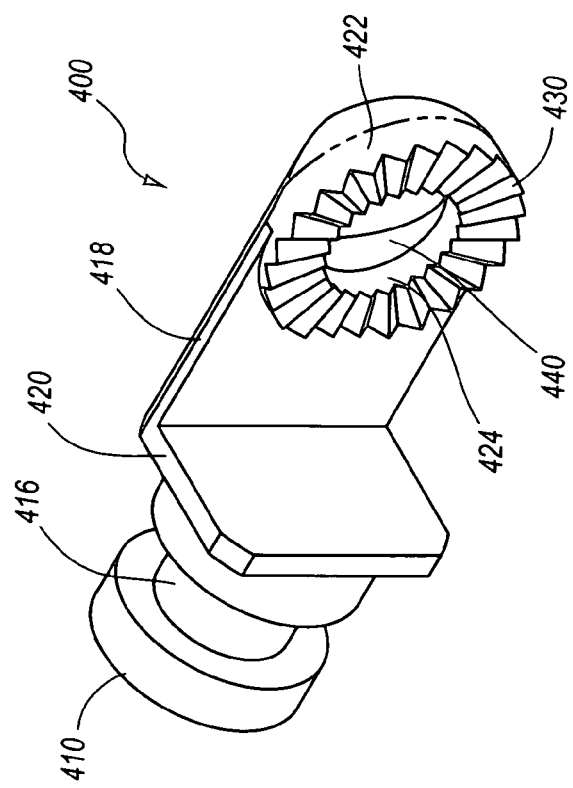
Figure 17A:
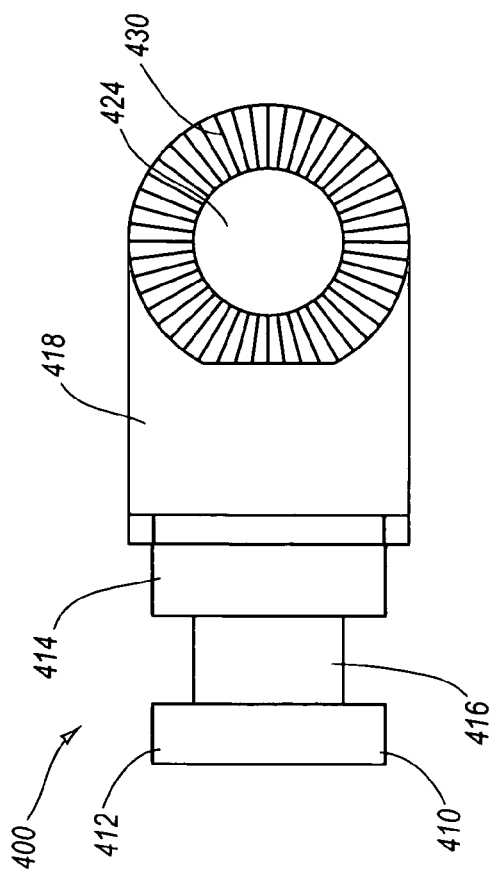
Figure 17C:
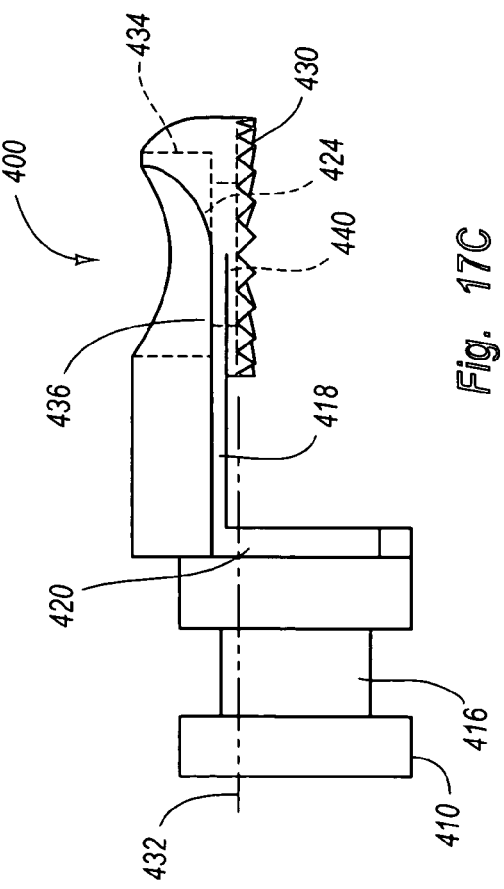

With reference now to FIG. 17, upper joint member 400 will now be discussed in additional detail. Upper joint member 400 may be configured similarly or identically to joint 300 of splint 10. As shown, upper joint member 400 comprises: (i) a cylindrical body 410 having a first end 412 and a second end 414 and an annular groove 416 therebetween; (ii) an extension member 418 extending from the cylindrical body 410, the extension member 418 having a first end 420 that is coupled to the second end 414 of the cylindrical body 410 and a second end 422 having an aperture 424 therein; and (iii) a circular array of teeth 430 on the second end 422 of member 418 extending concentrically about the aperture 424, such that the aperture 424 extends through the teeth 430 and the second end 422 of extension member 418. Extension member 418 extends away from cylindrical body 410 such that the longitudinal axis of extension member 418 is aligned with the longitudinal axis 432 (e.g., parallel to, or along the same axis) of cylindrical body 410. Hence, teeth 430 are oriented transversely to the longitudinal axis 432 of cylindrical body 410.

Aperture 424 defines a chamber 434 having an internal ridge 436 on which the head 438 of bolt 406 rests when joint 380 is assembled. Chamber 434 further comprises a passageway 440 through which the body 442 of bolt 406 extends during assembly.

Figure 18B:
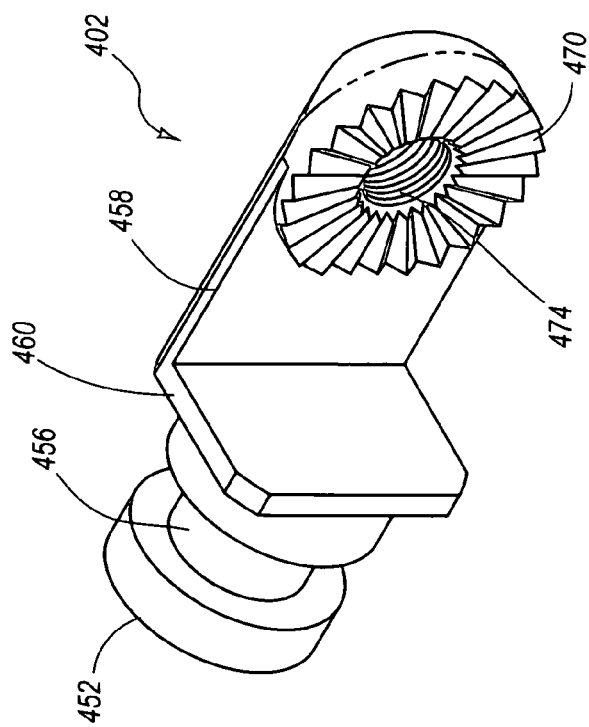
Figure 18A:
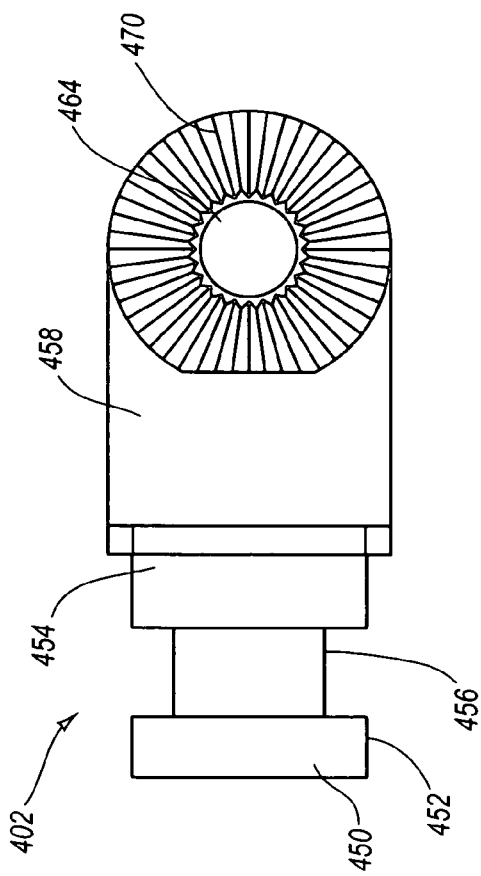
Figure 18C:
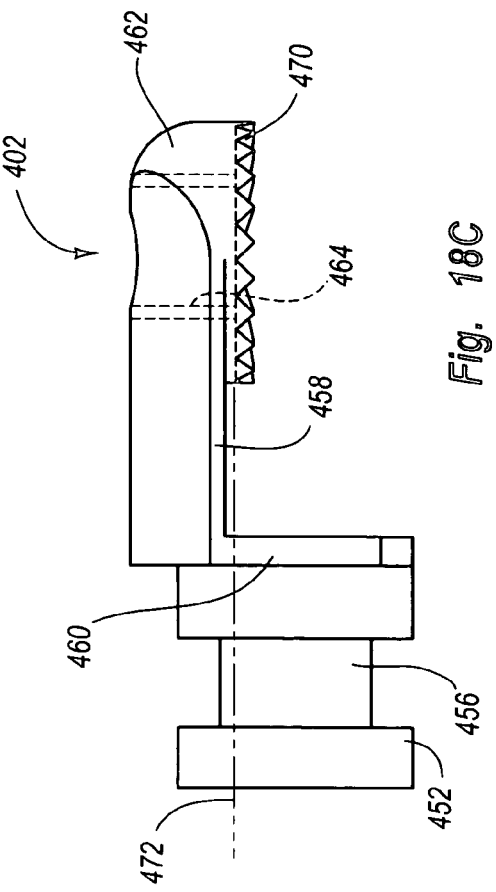

As illustrated now in FIG. 18, lower joint member 402 comprises: (i) a cylindrical body 450 having a first end 452 and a second end 454 and an annular groove 456 therebetween; (ii) an extension member 458 extending from the cylindrical body 410, the extension member 458 having a first end 460 that is coupled to the second end 454 of the cylindrical body 450 and a second end 462 having an aperture 464 therein; and (iii) a circular array of teeth 470 on the second end 462 of member 458 extending concentrically about the aperture 464, such that the aperture extends through the teeth 470 and the second end 462 of extension member 458. Extension member 458 extends away from cylindrical body 450 such that the longitudinal axis of extension member 458 is aligned (e.g., parallel to, or along the same axis) with the longitudinal axis 472 of cylindrical body 450. Hence, teeth 470 are oriented transversely to the longitudinal axis 472 of cylindrical body 450. Aperture 464 defines a threaded passageway 474 through which the body 442 of bolt 406 extends during assembly.

Figure 19B:
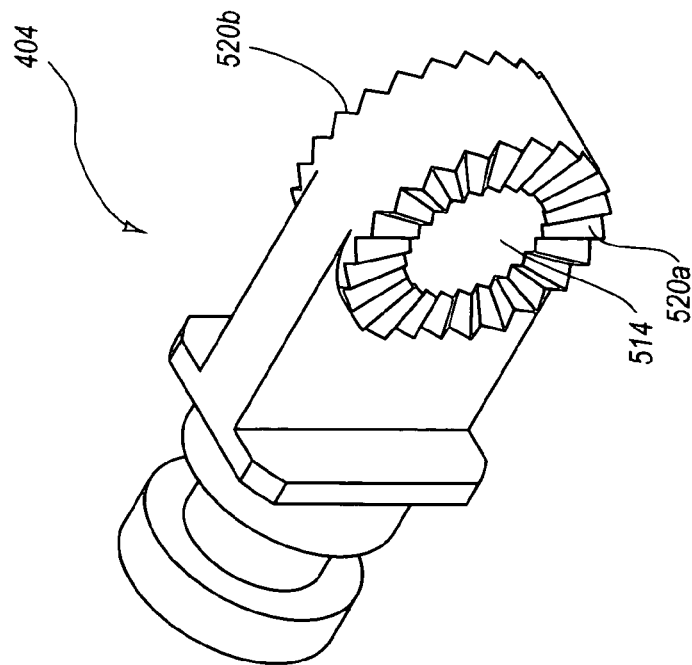
FIGS. 19A-C illustrate top, side perspective, and side views, respectively, of a central member of the three part joint of the splint illustrated in FIGS. 15 and 16.
Figure 19A:
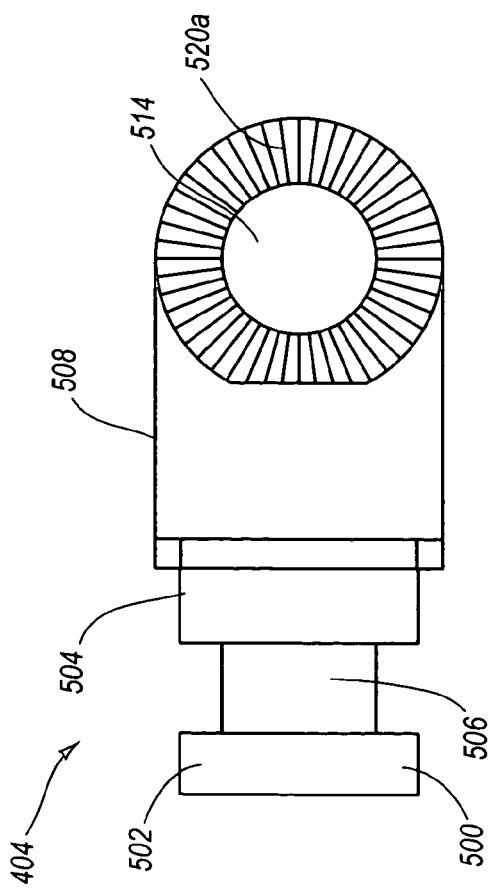
Figure 19C:
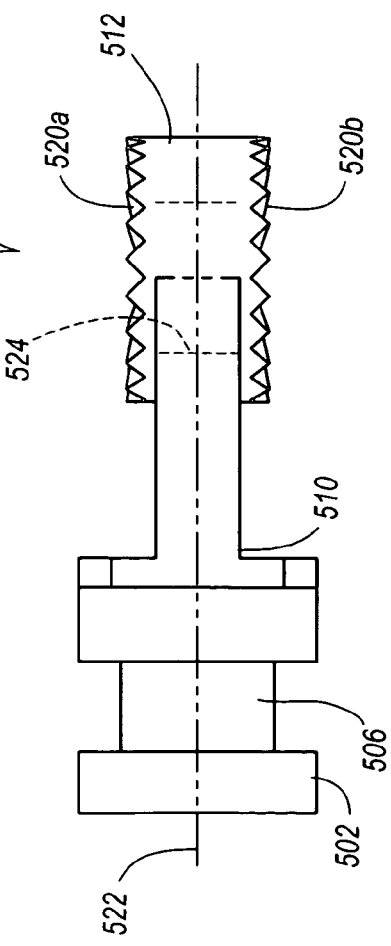

As illustrated now in FIG. 19, middle joint member 404 comprises: (i) a cylindrical body 500 having a first end 502 and a second end 504 and an annular groove 506 therebetween; (ii) an extension member 508 extending from the cylindrical body 500, the extension member 508 having a first end 510 that is coupled to the second end 504 of the cylindrical body 500 and a second end 512 having an aperture 514 therein; and (iii) first and second circular arrays of teeth 520a, 520b on opposing sides of the second end 512 of member 508 extending concentrically about the aperture 514, such that the aperture 514 extends through the teeth 520a-b and the second end 512 of extension member 508. Extension member 508 extends away from cylindrical body 500 such that the longitudinal axis of extension member 508 is aligned with the longitudinal axis 522 (e.g., parallel to, or along the same axis) of cylindrical body 500. Hence, teeth 520a-b are oriented transversely to the longitudinal axis 522 of cylindrical body 500. Aperture 514 defines a passageway 524 through which the body 442 of bolt 406 extends during assembly.

The cylindrical bodies of joint members 400, 402, 404 are received in mating relationship within respective chambers in main bodies 384, 386, 388. Thus, each of the joint members 400, 402, 404 has (i) a cylindrical body at a first end thereof which adjustably couples to a respective main body; and (ii) an aperture at a second end thereof about which teeth extend.

During assembly, as illustrated in FIG. 16, the teeth of each joint member 400, 402, 404 are aligned and placed adjacent each other in mating relationship, such that the apertures extending through each joint member 400, 402, 404 are aligned. Bolt 406 is then extended through upper joint member 400, then through middle joint member 404 and threaded into lower joint member 402, thereby retaining joint members 400, 402, 404 in a fixed, aligned position with respect to each other. Upon desiring to adjust the orientation of one joint member with respect to the other, bolt 406 is loosened and the joint members are realigned (i.e., the teeth are realigned with respect to each other), after which the bolt 406 is replaced and tightened.

The circular array of teeth of the upper member 400 is sized and configured to align with the first circular array of teeth 520a on the middle joint member 404, and the circular array of teeth of the lower joint member 402 is sized and configured to align with the second circular array of teeth 502b of the middle joint member 404, thereby aligning the apertures of the upper, middle, and lower joint members, allowing the connecting member, e.g., bolt 406, to extend therethrough.

Each of the cylindrical bodies 410, 450, 500 of respective joint members 400, 402, 404 are selectively, adjustably coupled to respective main bodies 384, 386, 388 (i.e., within mating chambers thereof) through the use of respective connectors such as screws 530, 532, 534, as discussed above with respect to splint 10, as illustrated in FIGS. 15 and 16. Optionally, lower screws may also be employed. Thus, in light of the use of cylindrical bodies 410, 450, 500, any of the respective main bodies 384, 386, 388 may be moved in a 360 degree range of motion with respect to three-part joint 382.

In the embodiment of FIGS. 15 and 16, at least one middle joint member is employed. In another embodiment, two or more middle joint members are employed, such that four, five, six or more main bodies may be used in an axial splint.

Figure 20:
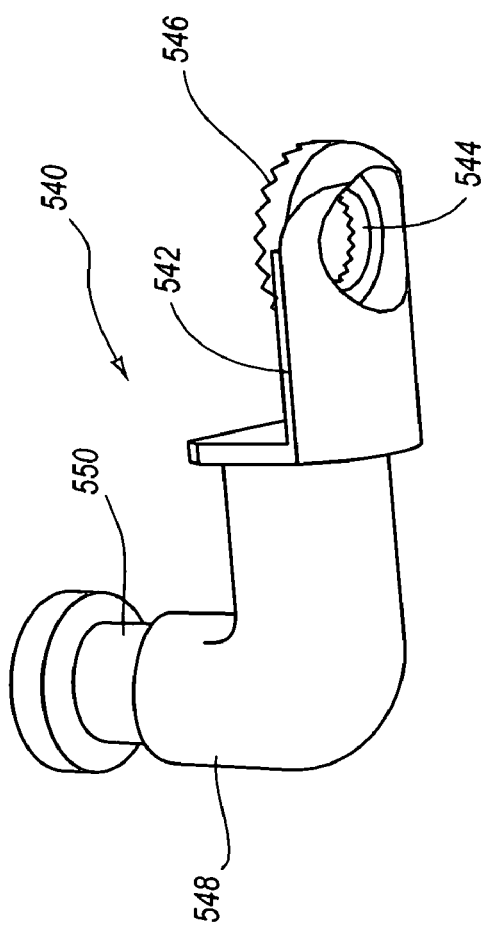
FIG. 20 illustrates an optional configuration of a joint member for possible use in any of the splints disclosed herein.

FIG. 20 illustrates yet another joint member 540 of the present invention that may be used in any of the splints described above. Joint member 540 has an extension member 542, aperture 544, and teeth 546 that are identical to the extension member, aperture, and teeth of joint member 300, but has a cylindrical body 548 that is coupled at an angle transverse to extension member 542. Cylindrical body 548 has an annular groove 550 therein, which may be coupled to a main body through the use of a screw, similar to the joint members discussed above. Thus, the joint members of the present invention may have curves or other configurations therein that enable their respective main bodies to be placed in difficult or complicated relationships with respect to bones and/or other main bodies.

Figure 21:
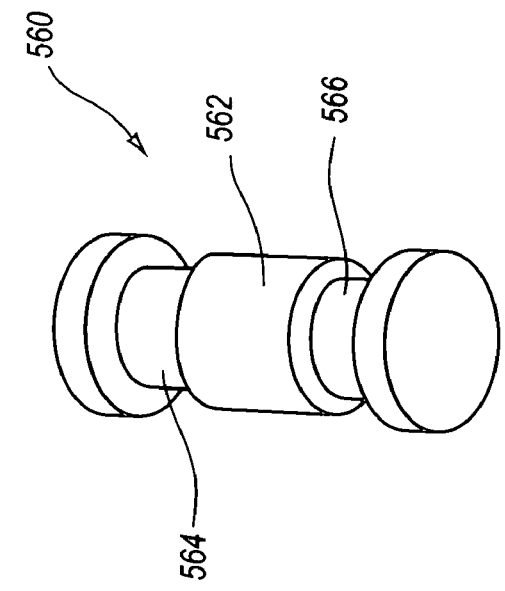
FIG. 21 illustrates an optional configuration of a joint member for possible use in any of the splints disclosed herein.

Further joint members may have a variety of different features or combinations of the foregoing members. In yet another embodiment, the joint is comprised of a single joint member 560 as shown in FIG. 21, wherein the joint member 560 comprises an elongate, cylindrical body 562 having first and second annular grooves 564, 566 at opposing ends thereof. Opposing ends of the joint member 560 are selectively mounted into main bodies through the use of screws, as discussed above with joint member 300, for example.

Figure 22:
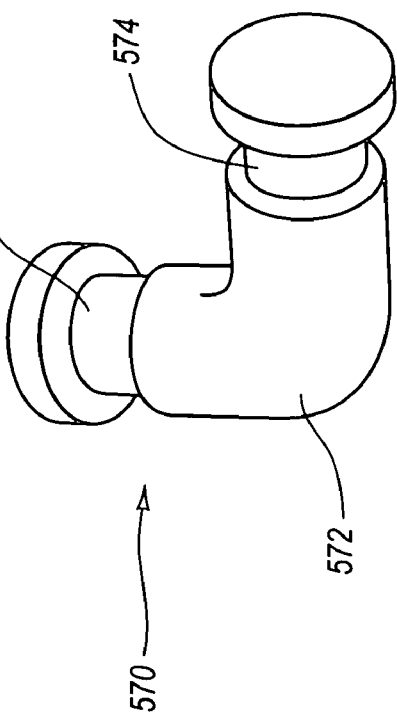
FIG. 22 illustrates an optional configuration of a joint member for possible use in any of the splints disclosed herein.

In yet another embodiment, the single joint member 570 has an angle therein as shown in FIG. 22, wherein the joint member 570 comprises an elongate cylindrical body 572 having first and second annular grooves 574, 576 at opposing ends thereof, wherein the elongate member is bent between the grooves. Opposing ends of the joint member 570 are selectively mounted into main bodies through the use of screws, as discussed above with joint member 300, for example.

The cylindrical bodies of the joint members and/or rear holder portions disclosed herein have a variety of different advantages, such as enabling convenient, selective coupling to a main body and convenient rotation in a 360 degree range of motion about each such cylindrical body. For example, the mounts of the present invention may be coupled to the main body or bodies of a respective splint prior to installation. Optionally, however, one or more bone connectors with one or more respective mounts thereon may first be coupled to one or more bones, after which the main body or bodies can be connected to a respective mount or mounts. This may be useful in a setting in which it is difficult to place one or more bone connectors in a desired location. This is possible because of the convenient coupling of a mount to a main body, or of one main body to another main body, through the use of the aforementioned cylindrical bodies, which conveniently couple to respective main bodies, as shown. Thus, during installation, the mount(s) may be first coupled to a main body or bodies, or may be first coupled, along with one or more bone connectors, to a bone or bones, after which the main body is coupled to the mount(s).

The splints of the present invention are useful in a variety of different settings. For example, in one embodiment, the splints of the present invention can be used for callous distraction, e.g., the splint is first employed to compress two portions of bone with respect to each other, then after a period of time, such as a week, one or more mounts on a splint is moved away from one or more other mounts, thereby distracting the bone(s), causing the bone to grow. According to one procedure, the bone is first cut, then reattached and compressed for a period of time, then lengthened slightly on a regular basis to grow the bone.

As one option, the mounts on the splint can be adjusted often, e.g., by moving ¼ millimeter apart four times per day for a week, or other amount of adjustment as desired. A fracture can be thus reduced by first compressing, then gradually distracting portions of a bone. These regular adjustments can be performed by the practitioner or patient.

In one embodiment, in order to achieve a desired thread ratio, one complete rotation of the lead screw is equal to one millimeter of translational movement of a mount along the axis of the screw.

Figure 23:
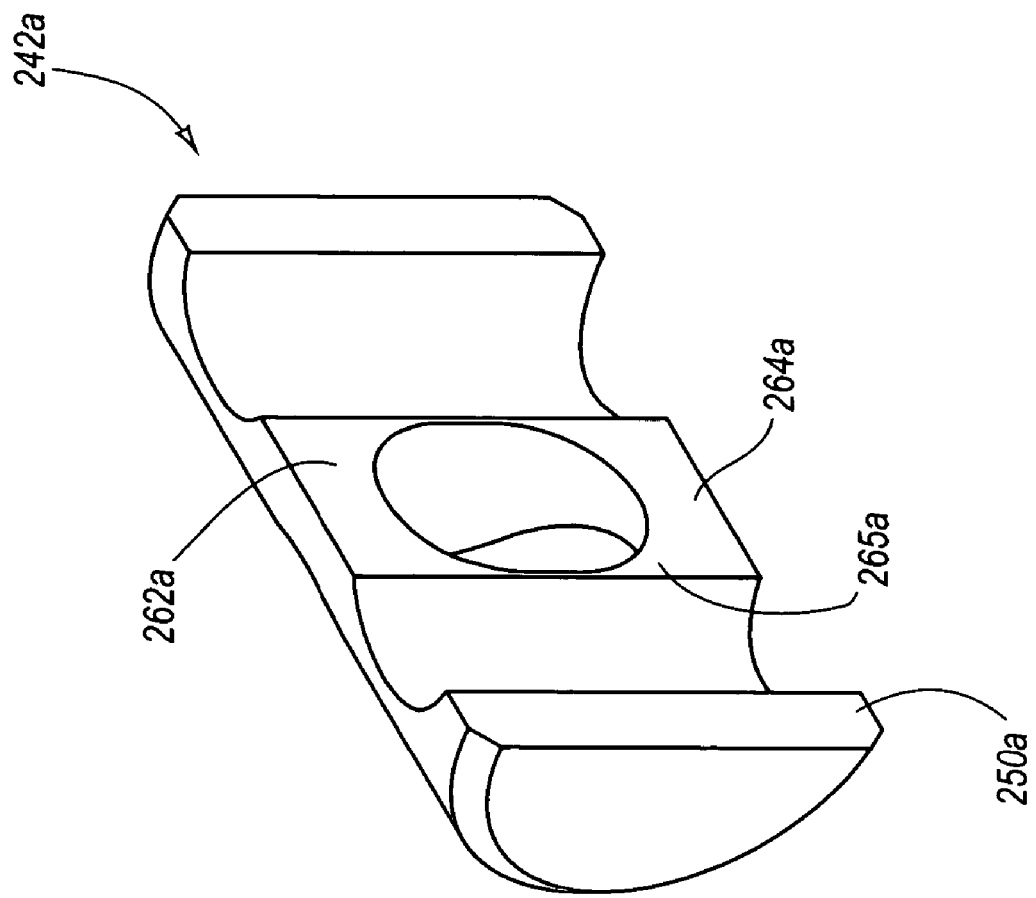
FIG. 23 illustrates an optional configuration of one part of a collar, which can be employed in any of the splints disclosed herein, the opposing part of the collar having, in one embodiment, the same configuration. The collar portion of FIG. 23 does not have the upper and lower ridges of the collar portion of FIG. 7, such that the face portion is flush, which is an optional configuration designed to simplify the machining process during manufacture.

FIG. 23 demonstrates another collar member 242a of the present invention that is similar to collar member 242 except that it does not have the upper and lower surface 262 and 264 in the interior thereof. Instead, the interior surface 250a of collar member 242a has upper and lower central surfaces 262a, 264a that are flush with an inner surface 265a of interior surface 250a, rather than having a notched portion.

FIGS. 24-28 illustrate optional grooves of the two-part collars of the present invention. Each groove can be used for a differently shaped bone connector, such as a screw. For example, collar member 242b features a pair of elongated ovoid grooves 580a-b which can be used to couple to bone connectors having small or large diameters. Collar member 242c features a pair of elongated semi-elliptical grooves 582a-b which can also be used to couple to bone connectors having small or large diameters. Collar member 242d features a pair of flattened triangular grooves 584a-b which can also be used to couple to bone connectors having a corresponding cross section. Collar member 242e features a pair of triangular grooves 586a-b which can also be used to couple to bone connectors having a corresponding cross section. Collar member 242f features a pair of hemi-hexogonal grooves 588a-b which can also be used to couple to bone connectors having a corresponding cross section.

Although mounts such as mounts 16, 18, and 20 are identified as possible mounts of the present invention, a variety of different mounts may be employed to connect a bone connector to a main body. Thus, a "mount" as referenced in this specification or the appended claims may be any material or structure that connects a bone connector to a splint main body.

Additional disclosure relating to the embodiments of the present invention is available in the U.S. patent applications filed on Mar. 18, 2005 and entitled "Adjustable Splint for Osteosynthesis," and "Adjustable Splint for Osteosynthesis with Modular Joint," each of which are incorporated herein by reference in their entirety.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An axial splint for osteosynthesis comprising:
a first main body;
a second main body;
a third main body;
a first bone connector;
a second bone connector;
a third bone connector;
a first mount coupled to the first main body, the first mount adapted to couple to the first bone connector;
a second mount coupled to the second main body, the second mount adapted to couple to the second bone connector;
a third mount coupled to the third main body, the third mount adapted to couple to the third bone connector; and
a joint extending from and coupling a first end of each of the first, second, and third main bodies to each other, the joint comprising:
a first joint member having a first end and a second end, the first end having a longitudinal axis that is substantially parallel to a longitudinal axis of the first main body, the first end of the first joint member comprising a cylindrical body having an annular groove therein for mounting within the first main body, the second end of the first joint member having an aperture extending therethrough;
a second joint member having a first end and a second end, the first end having a longitudinal axis that is substantially parallel to a longitudinal axis of the second main body, the first end of the second joint member comprising a cylindrical body having an annular groove therein for mounting within the second main body, the second end of the second joint member having an aperture extending therethrough;
a third joint member having a first end and a second end, the first end having a longitudinal axis that is substantially parallel to a longitudinal axis of the third main body, the first end of the third joint member comprising a cylindrical body having an annular groove therein for mounting within the third main body; and
a connecting member sized and configured to extend through the apertures of the first and second joint members, and into third joint member to align the second ends of the first, second, and third joint members and couple the first, second, and third joint members together, wherein each of the first, second, and third joint members and the connecting member is adapted to maintain the respective first, second, and third main bodies at a constant distance from a central axis of the joint, each of the first, second, and third main bodies being independently rotatable about the central axis of the joint, and wherein each of the first, second, and third main bodies can be independently adjusted back and forth in the same plane, wherein the first joint member, the second joint member, and the third joint member are adjustably connected, wherein the second joint member is configured to be sandwiched between the first and second joint members; and wherein each of the first, second and third joint members comprises a set of teeth.

2. A splint for osteosynthesis as recited in claim 1 wherein the first main body has a first end and a second end, the first main body having a longitudinal axis, the first main body also having a slot therein, the slot having a first end and a second end, the slot also having a longitudinal axis that is substantially parallel to the longitudinal axis of the first main body;

a screw having a first end and a second end, the screw being rotatably positioned entirely within an interior portion of the slot, the first end of the screw being rotatably coupled to the first end of the first main body and the second end of the screw being retained within the interior portion of the slot, wherein each of the first and second ends of the screw are maintained entirely within the interior portion of the slot when the screw is rotated within the slot; and wherein a portion of the first mount extends into the slot of the first main body and is movably mounted on the screw such that rotation of the screw moves the mount along the length of the screw between the first and second ends of the slot.

3. An adjustable splint as recited in claim 2, wherein the second end of the screw is retained within the slot by a retaining member positioned adjacent a terminal surface of the second end of the screw.

4. A splint as recited in claim 2 wherein the screw is rotatably coupled at one end thereof to one portion of the first main body and is movably maintained at the other end thereof within the first main body through the use of a split retaining ring.

5. A splint as recited in claim 4 wherein the retaining ring is mounted within a groove in the slot of the first main body.

6. An adjustable splint as recited in claim 2, wherein the first main body adjustably couples to the joint for coupling the first main body to the second and third main bodies.

7. An axial splint as recited in claim 1, wherein each set of teeth is configured to mate with a corresponding set of teeth on another joint member.

8. A splint as recited in claim 1, wherein the teeth of the first joint member are oriented transversely to a longitudinal axis of a cylindrical body of the first joint member.

9. An axial splint as recited in claim 1, wherein the cylindrical body of each of the first, second, and third joint members is adapted for mounting within a respective main body.

10. An axial splint as recited in claim 1, wherein the first bone connector comprises a screw or a bolt.

11. A splint as recited in claim 1, wherein the first mount is coupled to the main body in at least one of a sliding relationship and a rotating relationship.

12. A splint as recited in claim 1, wherein the first main body has a first end and a second end, the first main body having a slot therein, and further comprising:

a lead screw having a first end and a second end, the lead screw being positioned within the slot, the first end of the lead screw being rotatably coupled to a first end of the main body and the second end of the lead screw being retained within the slot, and the first mount being movably mounted on the lead screw.

13. An adjustable splint as recited in claim 12, wherein the second end of the lead screw is retained within the slot by a retaining member positioned adjacent a terminal surface of the second end of the lead screw.

14. A splint as recited in claim 1, wherein the first joint member, the second joint member, and the third joint member are adjustably connected through the use of the connecting member.

15. A splint as recited in claim 1, wherein the first, second, and third main bodies are each selectively rotatable.

16. A splint as recited in claim 1, wherein the connecting member is a bolt.

17. A splint as recited in claim 1, wherein the teeth of each joint member comprise a circular array of teeth.

18. A splint as recited in claim 1, wherein the teeth on each joint member extend concentrically about an aperture extending therethrough.

19. An axial splint for osteosynthesis comprising:
a first main body;
a second main body;
a third main body;
a first bone connector;
a second bone connector;
a third bone connector;
a first mount coupled to the first main body, the first mount adapted to couple to the first bone connector;
a second mount coupled to the second main body, the second mount adapted to couple to the second bone connector;
a third mount coupled to the third main body, the third mount adapted to couple to the third bone connector; and
a joint extending from and coupling a first end of each of the first, second, and third main bodies to each other, the joint comprising:
a first joint member having a first end and a second end, the first end having a longitudinal axis that is substantially parallel to a longitudinal axis of the first main body, the first end of the first joint member comprising a cylindrical body having an annular groove therein for mounting within the first main body, the second end of the first joint member having an aperture extending therethrough;
a second joint member having a first end and a second end, the first end having a longitudinal axis that is substantially parallel to a longitudinal axis of the second main body, the first end of the second joint member comprising a cylindrical body having an annular groove therein for mounting within the second main body, the second end of the second joint member having an aperture extending therethrough;
a third joint member having a first end and a second end, the first end having a longitudinal axis that is substantially parallel to a longitudinal axis of the third main body, the first end of the third joint member comprising a cylindrical body having an annular groove therein for mounting within the third main body; and
a connecting member sized and configured to extend through the apertures of the first and second joint members, and into third joint member to align the second ends of the first, second, and third joint members and couple the first, second, and third joint members together, wherein each of the first, second, and third joint members and the connecting member is adapted to maintain the respective first, second, and third main bodies at a constant distance from a central axis of the joint, each of the first, second, and third main bodies being independently rotatable about the central axis of the joint, and wherein each of the first, second, and third main bodies can be independently adjusted back and forth in the same plane, wherein a circular array of teeth extends concentrically about the aperture on at least one side of the second end of the first joint member, a first circular array of teeth extends concentrically about the aperture on a first side of the second end of the second joint member; and wherein a second circular array of the teeth extends concentrically about the aperture on a second side of the end of the second joint member; and wherein a circular array of the teeth extends concentrically about the aperture on at least one side of the second end of the third joint member; and wherein the circular array of teeth of the first member is sized and configured to align with the first circular array of teeth on the second joint member, and the circular array of teeth of the third joint member is sized and configured to align with the second circular array of teeth of the second joint member, thereby facilitating selective positioning of the first, second, and third main bodies relative to one another and about the central axis of the joint.

20. A splint as recited in claim 19, wherein the cylindrical body of each of the first ends of the first, second, and third joint members facilitates rotation of the first, second, and third main bodies about the longitudinal axis of the cylindrical bodies of the first, second, and third joint members.

21. A splint as recited in claim 20, wherein the annular groove is configured to receive a connector therein, the connector being extended from a main body into the annular groove, 22. A splint as recited in claim 19, wherein the connecting member is a bolt.

23. A splint as recited in claim 19, wherein the main bodies are each selectively rotatable.

24. A splint as recited in claim 19, wherein the connecting member is a bolt.

25. A splint as recited in claim 19, wherein each of the main bodies can be selectively rotated about an axis of the respective main body.

* * * * *

UNITED STATES PATENT AND TRADEMARK OFFICE
CERTIFICATE OF CORRECTION

PATENT NO. : 7,575,575 B2  
APPLICATION NO. : 11/084056  
DATED : August 18, 2009  
INVENTOR(S) : Olsen et al.

Page 1 of 1

It is certified that error appears in the above-identified patent and that said Letters Patent is hereby corrected as shown below:

Column 5  
Line 8, change "16, 18 20" to --16, 18, 20--

Column 6  
Line 23, change "housing 74" to --housing 70--  
Line 39, change "slot 84" to --annular groove 84--

Column 7  
Line 18, change "distal front chamber 112," to --second top aperture 102,--  
Line 40, change "lead screw 70" to --lead screw 60--

Column 11  
Line 46, change "U-shaped member 190" to --U-shaped member 272--

Column 12  
Lines 12, change "aperture 102" to --hollow chamber 110--

Column 14  
Line 38, change "bodies 10" to --bodies 12, 14--  
Line 39, change "main body 10" to --main body 12--

Column 15  
Lines 14-15, change "joint 380" to --joint 382--

Column 16  
Line 12, change "teeth 502b" to --teeth 520b--

Column 17  
Line 59, "hemi-hexogonal" to --hemi-hexagonal--

Signed and Sealed this

Twelfth Day of January, 2010

David J. Kappos  
*Director of the United States Patent and Trademark Office*